US007793217B1

(12) United States Patent
Kim et al.

(10) Patent No.: US 7,793,217 B1

(45) Date of Patent: Sep. 7, 2010

(54) SYSTEM AND METHOD FOR AUTOMATED REPORT GENERATION OF OPHTHALMIC EXAMINATIONS FROM DIGITAL DRAWINGS

(76) Inventors: Young Kim, 13103 Frog Hollow Ct., Herndon, VA (US) 20171; Ken Lee, 2603 Hannah Farm Ct., Oakton, VA (US) 22124; Imran Noor Chaudhri, 10801 Brickyard Ct., Potomac, MD (US) 20854

( * ) Notice: Subject to any disclaimer, the term of this patent is extended or adjusted under 35 U.S.C. 154(b) by 1046 days.

(21) Appl. No.: 11/202,371

(22) Filed: Aug. 12, 2005

Related U.S. Application Data

(63) Continuation-in-part of application No. 11/175,410, filed on Jul. 7, 2005.

(60) Provisional application No. 60/585,568, filed on Jul. 7, 2004, provisional application No. 60/600,776, filed on Aug. 12, 2004.

(51) Int. Cl.
*G06F 17/00* (2006.01)

(52) U.S. Cl. .................................................... 715/255

(58) Field of Classification Search ................. 715/200, 715/234, 255, 243

See application file for complete search history.

(56) References Cited

U.S. PATENT DOCUMENTS

| | | | | |
|---|---|---|---|---|
| 5,179,651 | A | 1/1993 | Taaffe et al. | |
| 5,327,341 | A * | 7/1994 | Whalen et al. | 705/3 |
| 5,581,460 | A * | 12/1996 | Kotake et al. | 705/3 |
| 5,732,221 | A * | 3/1998 | Feldon et al. | 705/3 |
| 6,032,120 | A | 2/2000 | Rock et al. | |
| 6,381,557 | B1 | 4/2002 | Babula et al. | |
| 6,524,245 | B1 | 2/2003 | Rock et al. | |
| 6,581,069 | B1 | 6/2003 | Robinson et al. | |
| 2002/0188896 | A1* | 12/2002 | Filteau et al. | 714/57 |
| 2003/0016850 | A1* | 1/2003 | Kaufman et al. | 382/128 |
| 2005/0010859 | A1* | 1/2005 | McDonough et al. | 715/500 |
| 2005/0021413 | A1* | 1/2005 | Berry et al. | 705/26 |
| 2005/0096530 | A1* | 5/2005 | Daw et al. | 600/408 |
| 2005/0107689 | A1* | 5/2005 | Sasano | 600/425 |
| 2005/0107690 | A1* | 5/2005 | Soejima | 600/425 |
| 2005/0120300 | A1* | 6/2005 | Schwager et al. | 715/513 |

(Continued)

OTHER PUBLICATIONS

Yannuzzi et al., Ophthalmic Fundus Imaging: Today and Beyond, Google 2004, pp. 511-524.*

(Continued)

*Primary Examiner*—Cong-Lac Huynh

(74) *Attorney, Agent, or Firm*—Edell, Shapiro & Finnan, LLC

(57) ABSTRACT

The present invention is a combined image viewing, drawing, and reporting system, which provides: an easy way to access digital images while creating a digital drawing; and an automated method of creating medical reports by translating the drawing data into standard reports. The present invention system provides automated medical drawings and creates medical reports as a result of translating drawing results. The system provides invaluable tools for drawing, diagnosing and treating ophthalmic and/or other types of diseases by generating an automated translation report based on the physician drawing. Customized reports (e.g., a medical drawing report, a referral note, a medical letter, billing based information, a proofsheet for the patient chart, etc.) can be added by the user. A physician can design a format for a report via system utility tools. The present invention may be a stand-alone system, and/or connected to a network.

49 Claims, 28 Drawing Sheets

U.S. PATENT DOCUMENTS

| | | | | |
|---|---|---|---|---|
| 2005/0197860 | A1 * | 9/2005 | Joffe et al. | 705/2 |
| 2005/0265588 | A1 * | 12/2005 | Gholap et al. | 382/128 |
| 2006/0064321 | A1 * | 3/2006 | Sasano et al. | 705/2 |
| 2006/0136269 | A1 * | 6/2006 | Fraser | 705/3 |
| 2006/0242143 | A1 * | 10/2006 | Esham et al. | 707/6 |
| 2006/0242149 | A1 * | 10/2006 | Richard | 707/8 |
| 2008/0071576 | A1 * | 3/2008 | Berry et al. | 705/2 |
| 2009/0048833 | A1 * | 2/2009 | Fritsch et al. | 704/235 |

OTHER PUBLICATIONS

Lim et al., A Web-based Collaborative System for Medical Image Analysis and Diagnosis, ACM 2001, pp. 93-95.*

Kim et al., A Solutiion to the Distribution and Standardization of Multimedia Medical Data in E-Health, ACM 2002, pp. 1-4.*

R. Long, LE Berman, GR Thoma, "Design Considerations for Wide Area Distribution of Digital X-Ray Images," PACS Design and Evaluation, Proc. SPIE, vol. 1899, Medical Imaging, 1993, pp. 383-394.

Daniel Ertman, "Oxalis: A Distributed, Extensible Ophthalmic Image Annotation System," Submitted to the Graduate Faculty of the School of Engineering in partial fulfillment of the requirements for the degree of Master of Science, University of Pittsburgh, 2003.

* cited by examiner

| | ModalityPat | ModalityPa | LastName | FirstName | MiddleNam | Sex | DOB | CreateDate | LastModifie | NextVisitDa | Pathology |
|---|---|---|---|---|---|---|---|---|---|---|---|
| | 005_555_3 | | Jones | VMC23 | dfasd | Other | 1/1/1900 | 10/15/2003 | 2/17/2004 | (null) | test |
| | import_test | frearad | Jones001 | VMC23001 | kkk | Other | 1/1/1900 | 1/14/2004 | 2/17/2004 | (null) | |
| | 1 | 1.2.3.4 | p4 | PATIENT_ | D | M | 1/15/1950 | (null) | 2/16/2004 | (null) | pat |
| | 1 | 1.2.3.4 | p4 | PATIENT_ | D | M | 1/15/1950 | (null) | 2/16/2004 | (null) | pat |
| | 1 | 1.2.3.4 | p4 | PATIENT_ | D | M | 1/15/1950 | (null) | 2/16/2004 | (null) | pat |

Total records: 5

```
<?xml version='1.0'?>

<ReportElement>
      <header>
            <title value="Sample report for the auto drawing"></title>
            <headerimage location="images/logo/anka_32x32a.gif"
align="left"></headerimage>
            <hospital name="Medicine Center" reportcategory="Clinic
note"></hospital>
            <primaryPhysician name="John Doe0 M.D., FACS" address="1234 fox ave,
sp, VA 12345" phone="123-123-1234" fax="123-321-4321"></primaryPhysician>
            <referringPhysician name="John Doe1 M.D., FACS" address="1234 fox
ave, sp, VA 12345" phone="123-123-1234" fax="123-321-4321"></referringPhysician>
            <attendingPhysician name="John Doe2 M.D., FACS" address="1234 fox
ave, sp, VA 12345" phone="123-123-1234" fax="123-321-4321"></attendingPhysician>
            <referringto name="John Smith M.D., FACS" address="1234 fox ave, sp,
VA 12345" phone="123-123-1234" fax="123-321-4321"></referringto>
      </header>
      <subject>
            <title>Clinic Note</title>
            <CC>Miki Mouse</CC>
            <to>John Smith M.D., FACS</to>
      </subject>
      <reason>
            <visit>Evaluation of macular changes and cataract extraction</visit>
            <evaluation>macular degeneration</evaluation>
            <illness></illness>
      </reason>
      <patient>
            <name>Joe, J, Smith</name> <!-- last, mid, first name -->
            <address>1616 Anderson Rd, Meclean, VA 22102 </address>
            <patientid>123456789</patientid>
            <visitdate>08/10/2004</visitdate>
            <phone>123.123.1234</phone>
            <dob>1/1/1930</dob>
            <race></race>
            <gender>male</gender>
            <location>1111</location>
            <documentnumber>doc#1234343241</documentnumber>
            <primaryprovider>Imran Chaudhri</primaryprovider>
            <otherprovider>Ken Lee</otherprovider>
            <note></note>
            <summary></summary>
            <patientnotice></patientnotice>
      </patient>
      <Patienthistory>
            <summary>Mr.someone is a 70 years old, Caucasian male here for
further evaluation
            of age-related macular degeneration. He is .....</summary>
      </Patienthistory>
      <medications>Procardia XL 30mg</medications>
      <allergies>Actifed</allergies>
      <majorfinding>
            <summary>Visual acuity without correction measures 20/400 OD and
20/200+1 OS.
```

FIG.18A

```
Pupilary reactions to light are normal and there is no
            afferent .... </summary>
            <drawingtranslation></drawingtranslation>
            <physicianimpression>250.5 Diabetes</physicianimpression>
      </majorfinding>
      <assessments>
            <summary>Ms.Somenoe has a history of neovascular AMD with a
disciform scar
            OD and non-neovascular AMD with central geographic atrophy OD.
....</summary>
      </assessments>
      <problemsdiagnosis>
      <problems></problems>
            <diagnosis></diagnosis>
      </problemsdiagnosis>
      <procedures>
            <summary>Color fundus photographs were obtained today to document
the above
            described clinical findings and for comparison at future following
visits.</summary>
      </procedures>
      <Immunizations>
            <summary>The images reveal atrophy and a disciform scar OD as well
as drusen OD,
            and central atrophy with drusen OS. the findings are consistent with
non-neovascular
            AMD OD and advanced non-neovascular AMD OS.</summary>
      </Immunizations>
      <plantreatment>
            <Plan>Discussed pseudoexfoliation and increased risk of cataract
surgery</Plan>
            <treatment></treatment>
      </plantreatment>
      <medicationchanges>
            <summary></summary>
      </medicationchanges>
      <NextSchedule>
            <returntoclinic>2days/sooner PRN, pre-op evaluation</returntoclinic>
            <schedule>phaco/IOL OD(topical anesthesia)</schedule>
            <visitedate>10/04/2004</visitedate>
      </NextSchedule>
      <sendletterto>
            <to>
                  <hospital>Anka clinic</hospital>
                  <name>Young, Kim, M.D.</name>
                  <address>1616 Anderson Rd, Mclean, VA 22102</address>
                  <fax>703-714-0701</fax>
                  <phone>703-714-0700</phone>
            </to>
            <cc>Lee, Ken. M.D.; Lee, Jennifer M.D.</cc>
            <subject>[paitent name]</subject>
            <letterid>ANK_LET#_001234</letterid>
            <Greetingheader>Dear</Greetingheader>
            <bodymessage>I asked someone to see you for evaluation of cataracts.
 ... so on..</bodymessage>
            <Greetingfooter>Best Regard</Greetingfooter>
```

FIG.18B

```
<digitalsignFileLocation>c:\sign\young.sign</digitalsignFileLocation>
            <lettercreator>Chaudhri, Imran, M.D.</lettercreator>
      </sendletterto>
      <othernote>
            <note>send email to lab to get lab test result.</note>
      </othernote>
      <reserved>
            <rsv>Please send letter to administration for the scheduling.</rsv>
      </reserved>

</ReportElement >
```

FIG.18C

| Medical | Sample report for the auto drawing |
|---|---|
| | John Doe, M.D. Professor of Ophthalmology, Vitreoretinal Service. Fairfax hospital<br>1616 Anderson Rd, McLean VA 22102, Phone 703-123-1234, Fax 703-123-1235 |

Medicine Center *Clinic note*

Patient Information

| | | | |
|---|---|---|---|
| Name | Joe, J, Smith | History: | 123456789 |
| Address | 1616 Anderson Rd,<br>Meclean, VA 22102 | Visit date: | 07/07/2004 |
| Phone: | 703 123 1234 | | |
| Dob: | 1/1/2930 | | |
| Race: | | Location: | 1111 |
| Gender: | Male | Document No: | Doc#123234dfaderqe4 |
| Primary provider: | John Doe0 M.D., FACS | CC: | Miki Mouse |
| Other provider: | John Smith M.D., FACS | | |

Reason for visit: Evaluation of macular changes and cataract

History of present illness:

Mr.someone is a 70 years old, Caucasian male here for further evaluation of age-related macular degeneration. He is .....

Medication:

Procardia XL 30mg

Allegies:

Actifed.

Major finding:

Visual acuity without correction measures 20/400 OD and 20/200+1 OS. Pupilary reactions to light are normal and there is no Afferent ....

Assessments:

Ms.Somenoe has a history of neovascular AMD with a disciform scar OD and non-neovascular AMD with central geographic atrophy OD. ....

Problems:

Diagnosis:

250.5 Diabetes

Procedures:

Color fundus photographs were obtained today to document the above described clinical findings and for comparison at future following visits.

Immunizations:

The images reveal atrophy and a disciform scar OD as well as drusen OD, and central atrophy with drusen OS. the findings are consistent with non-neovascular AMD OD and advanced non-neovascular AMD OS

Plan/Treatment:

Discussed pseudoexfoliation and increased risk of cataract surgery

Medication changes:

Next schedule:

| | |
|---|---|
| Return to clinic: | 2days/sooner PRN, pre-op evaluation |
| Schedule: | phaco/IOL OD(topical anesthesia) |
| Next visit date: | 10/1/2005 |

CC List:

Lee, Ken. M.D.
Lee, Jennifer M.D.

Provider:

John Doe. M.D.

FIG.19

Paul Anka, M.D.
TYSON'S RETINA SPECIALISTS
1616 Anderson Road, Suite 108
Mclean, VA 22102
703.714.0700

May 12, 2005

Lee Davis, M.D.
123 Chain Bridge Road
McLean, VA 22102

RE: John Smith ID: 1234567

Dear Lee,

Thank you for referring John Smith for the evaluation of macular changes OS. The pupils were dilated and an extended ophthalmoscopy revealed: A few drusen are noted in the posterior pole OD. Macular edema is noted primarily temporal and inferotemporal to the foveal center OS. An inferotemporal branch retinal vein occlusion is present with microaneurysms. I have included these drawing and several key images below:

OD 5/12/2005

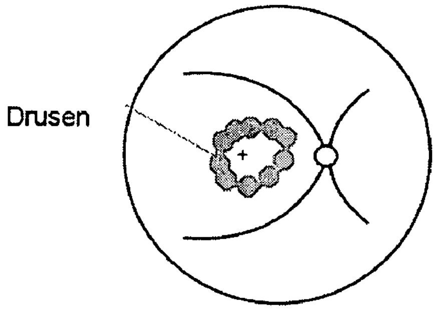

OS 5/12/2005

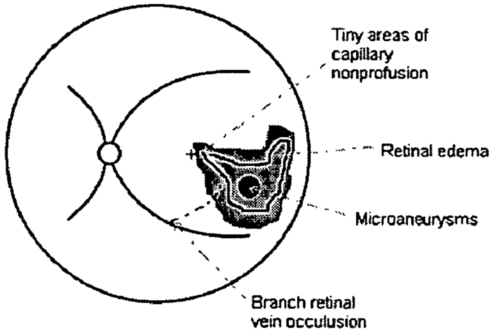

OS 5/12/2005

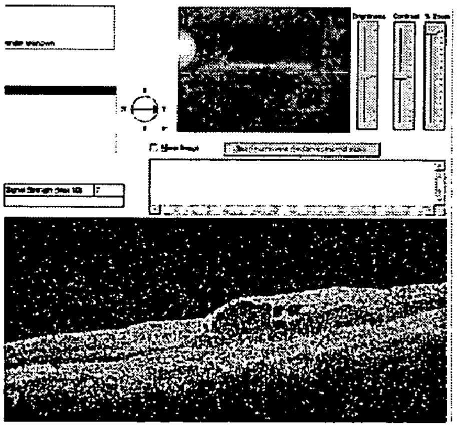

OS 5/12/2005

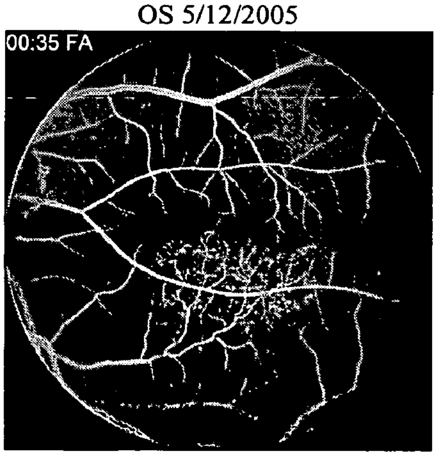

FIG.20A

Mr. John Smith has had a branch retinal vein occlusion of uncertain duration OS. This is associated with significant cystoid macular edema. He has not had any significant response to grid laser photocoagulation treatment OS. I have therefore recommended an intravitreal triamcinolone injection OS.

Lee, thank you again for the opportunity to share in the care of your patient.

Best regards,

Paul Anka, M.D.

FIG.20B

Drawing history

| Load | p123456 | 2004-Jun-10 | Dr. John Dow | Retina-Map-Form1 | Some translation comes here---- |
| Load | p123456 | 2004-Jun-10 | Dr. John Dow | Retina-Map-Form1 | Some translation comes here---- |
| Load | p123456 | 2004-Jun-10 | Dr. John Dow | Retina-Map-Form1 | Some translation comes here---- |
| Load | p123456 | 2004-Jun-10 | Dr. John Dow | Retina-Map-Form1 | Some translation comes here---- |
| Load | p123456 | 2004-Jun-10 | Dr. John Dow | Retina-Map-Form1 | Some translation comes here---- |
| Load | p123456 | 2004-Jun-10 | Dr. John Dow | Retina-Map-Form1 | Some translation comes here---- |

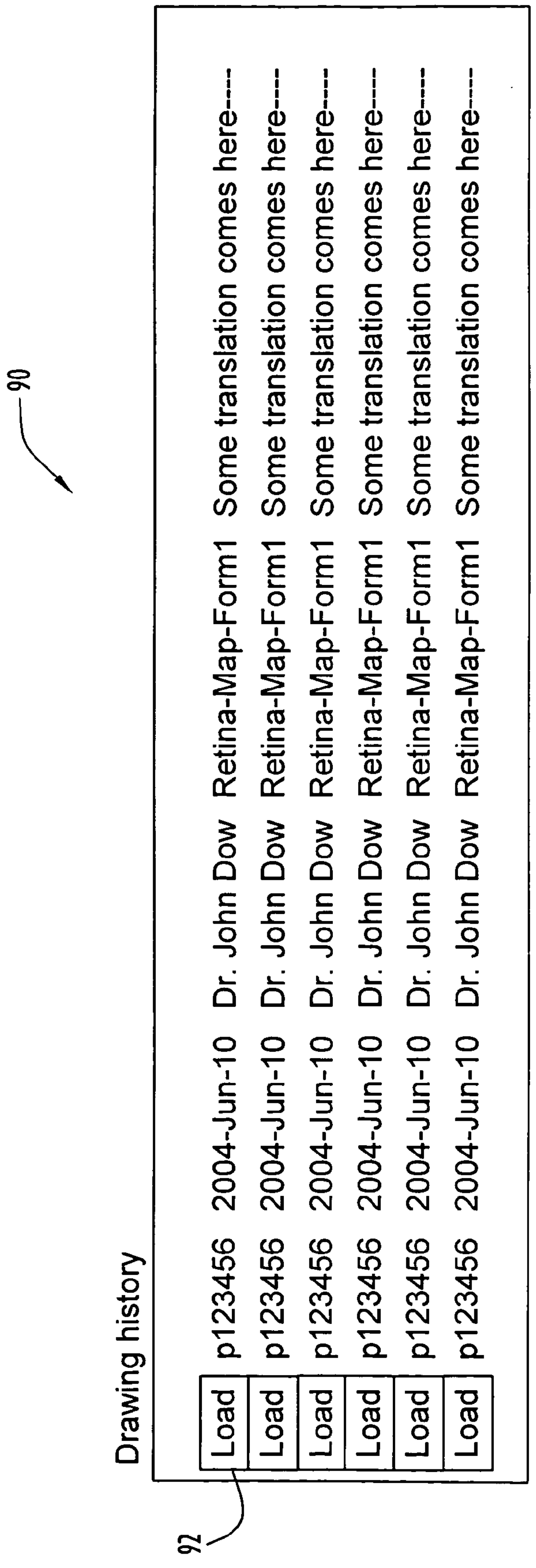

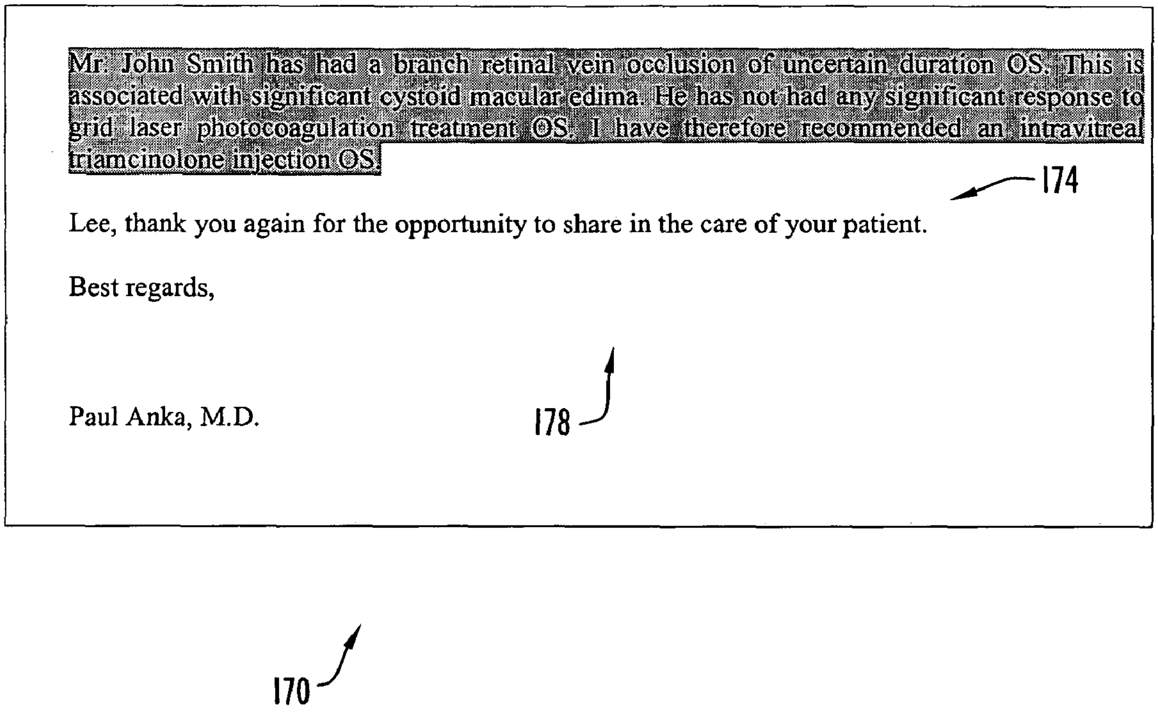

Mr. John Smith has had a branch retinal vein occlusion of uncertain duration OS. This is associated with significant cystoid macular edima. He has not had any significant response to grid laser photocoagulation treatment OS. I have therefore recommended an intravitreal triamcinolone injection OS.

Lee, thank you again for the opportunity to share in the care of your patient.

Best regards,

Paul Anka, M.D.

FIG.23B

SYSTEM AND METHOD FOR AUTOMATED REPORT GENERATION OF OPHTHALMIC EXAMINATIONS FROM DIGITAL DRAWINGS

CROSS-REFERENCE TO RELATED APPLICATIONS

This application is a Continuation-in-Part of U.S. patent application Ser. No. 11/175,410, entitled "System and Method for Efficient Diagnostic Analysis of Ophthalmic Examinations" and filed Jul. 7, 2005, which claims priority from U.S. Provisional Patent Application Ser. No. 60/585,568, entitled "System and Method for Efficient Diagnostic Analysis of Ophthalmic Examinations" and filed Jul. 7, 2004. In addition, the present application claims priority from U.S. Provisional Patent Application Ser. No. 60/600,776, entitled "System and Method for Automated Report Generation of Ophthalmic Examinations from Digital Drawings" and filed Aug. 12, 2004. The disclosures of the aforementioned patent applications are incorporated herein by reference in their entireties.

BACKGROUND OF THE INVENTION

1. Technical Field

The present invention relates generally to the field of medical reporting systems. More particularly, the present invention relates to a digital medical reporting system designed to allow ophthalmologists to automatically generate various patient reports from ophthalmic drawings based on manual evaluation of the interior of the eye (Opthalmoscopy) and/or other images generated from image capture stations. The present invention system enables ophthalmologists to create a medical drawing and to automatically provide annotations on those drawings to efficiently diagnose patients based on examinations. The present invention system further automatically generates several types of medical examination reports (e.g., billing reports for insurance companies, a proofsheet of an examination to be included in a patient chart, a referral letter to other physicians, etc.).

2. Discussion of Related Art

Currently, there are several digital capture stations that can also be used for ophthalmic diagnosis and that enhance the ability of physicians to create drawings. These capture stations include, but are not limited to, the following: Fundus Cameras for angiography, color photos, and red free photos; Ultrasound; Optical Coherence Tomography; Slit-lamp photography; Corneal Topography; and Scanning Laser Opthalmoscope. These capture stations complement one another and offer the ophthalmologist a range of techniques for imaging particular diseases.

Further, there are currently several drawing systems allowing physicians to create digital drawings. These drawing programs generate stand-alone digital images, which can then be associated with patient reports in an electronic medical record system (EMR). The most common ways to generate reports include:

(1) Writing out the report by hand;

(2) Filling out a pre-printed template by hand;

(3) Dictating a complete custom report;

(4) Dictating short notes to customize a digital template; and (5) Selecting choices and typing in short notes to customize a digital template.

Physicians spend a considerable amount of time using the above methods to generate standard reports, such as an Opthalmoscopy (drawing) report, a referral letter, and a billing report. The current physician workflow is illustrated in FIG. 1. Specifically, the physician performs a manual examination of the eye at step 10. If the patient is a repeat patient or has already had images taken, then the physician logs into the examination database or opens the paper examination chart at step 11, and retrieves and reviews existing examinations at step 12. The physician logs into the drawing program or obtains a paper drawing template at step 13. The physician subsequently creates and saves the drawing at step 14. Finally, the physician logs into the reporting system or obtains a paper report template at step 15 and creates the report at step 16 using one of the mechanisms described above. The examination is completed at step 17.

SUMMARY OF THE INVENTION

The present invention is a system that provides a solution to the need for manually generating reports by automating the report generation from the required digital drawings. The present invention is a combined image viewing, drawing, and reporting system, which provides: (1) an easy way to access digital images while creating the digital drawing; and (2) an automated method of creating medical reports by translating the drawing data into standard reports.

The present invention drawing and reporting system provides automated medical drawings and creates medical reports as a result of translating drawing results to reduce the huge amount of physician practice time diverted to those tasks. The system provides invaluable tools for drawing, diagnosing and treating ophthalmic and/or other types of diseases by generating an automated translation report based on the physician drawing. This allows physicians to draw more detailed and accurate medical annotations based on measurements from actual patients medical pictures.

Correct detail and an accurate annotation list enable several medical reports to be generated by automated translation technology. Customized reports (e.g., a medical drawing report, a referral note, a medical letter, billing based information, a proofsheet for the patient chart, etc.) can be added by the user. A physician can design a format for a report via system utility tools. Once the physician completes the customizing report template, this new report is automatically created immediately after completion of the drawing. As a result of using the present invention system, physicians save tremendous amounts of practice time, have very accurate drawing annotations and create automated reports based on their preferences.

The drawing and reporting systems of the present invention complement one another and offer the physician a range of techniques for imaging particular diseases. The present invention may be a stand-alone system, and/or connected to a network for communication with other systems (e.g., a central database and web server system, etc.) to share patient and examination information.

The present invention further provides several advantages. In particular, the present invention enables physicians or other users to search patient examinations and select photographs, composite images or predefined templates and draw on the selected items to identify problematic areas for diagnosis purposes. Previous drawings may be searched and edited to create new updated drawings and findings during patient progress. The system further provides the ability to modify the view of the selected item. For example, the system may include a zoom feature to zoom in and zoom out to different template levels (e.g. disk only, macula only, posterior segment only, etc.).

Further, new drawing elements or symbols along with their associated information (e.g., text, category, type) may be created by users to assist in identification of problematic areas on the selected item (e.g., photograph, image or template). The system enables rapid selection and placement of drawing elements on the selected item, where the drawing elements may represent positive and/or negative medical findings. The drawing elements may further be associated with element modifiers to enable the drawing elements to identify a combination of problems/findings within a desired area on the selected item. Moreover, a particular drawing element may be ascertained by a search for those elements via corresponding textual descriptions. The present invention system automatically maintains a most recently used drawing element symbol window and a most frequently used drawing element symbol window for each disease category to enable rapid element selection and placement on the selected item. In addition, the present invention system provides pre-defined element drawing behaviors (e.g. scaling arcs, radial arcs, encircling elements, automatic orientation towards the center, automatic circular element closure, etc.) to assist a user in drawing on the selected item.

With respect to automatic translation of user drawings on a selected item and/or report generation, the present invention system enables rapid creation of new report templates to provide customized reports, where the drawing elements are translated to textual reports based on the report templates. Positive and/or negative medical findings may be presented on the templates with automatic indication of finding locations. The specificity of the finding location information may be varied by a user. For example, the specificity of the location information may be set to a detailed location (e.g., between 1 and 2 o'clock of the posterior region), a general area (e.g., superior temporal posterior region, etc.), or no location information. In addition, the present invention system may automatically add images or drawings to generated reports.

The above and still further features and advantages of the present invention will become apparent upon consideration of the following detailed description of specific embodiments thereof, particularly when taken in conjunction with the accompanying drawings wherein like reference numerals in the various figures are utilized to designate like components.

BRIEF DESCRIPTION OF THE DRAWINGS

FIGS. 18A-18C are an illustration of an exemplary report template used to generate reports according to the present invention.

FIG. 19 is an illustration of an exemplary report produced by the present invention system.

FIGS. 20A-20B are an illustration of an exemplary letter produced by the present invention system.

FIG. 21 is a schematic illustration of an exemplary graphical user screen for selection of previous physician drawings according to the present invention.

FIGS. 23A-23B are a schematic illustration of an exemplary graphical user screen for editing a generated report according to the present invention.

DETAILED DESCRIPTION OF THE PREFERRED EMBODIMENTS

Figure 3:
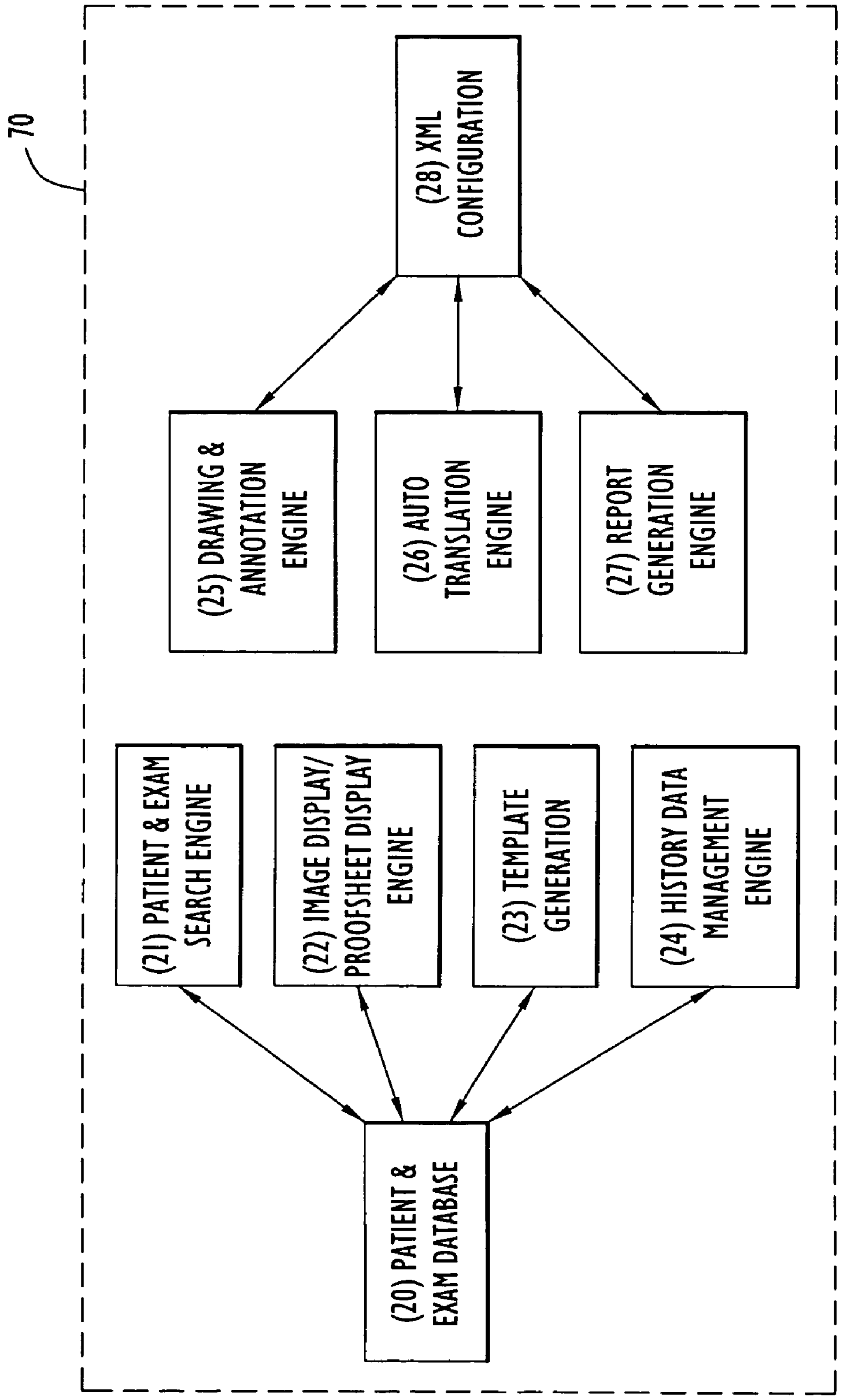
FIG. 3 is a block diagram of the present invention system.

The opthalmology system according to the present invention is illustrated in FIG. 3. Specifically, the system includes a patient and examination database 20, a patient and exam search module 21, an image display module 22, a template generation module 23, a history data management module 24, a drawing and auto annotation module 25, an auto translation module 26, a report generation module 27 and an XML configuration database 28. Each of these modules is described below. The system is preferably implemented by a computer system (e.g., personal computer, etc.) 70 including a Windows operating system, a SQL Server 2000 database management system and software (e.g., modules 21-27 described above) that may be complied and executed on the system. By way of example only, the computer system is implemented by one or more server computer systems available from Dell, Inc. and executing Windows Server 2000 software. The system may alternatively be implemented on a Tablet PC, NoteBook PC and/or Desktop PC with any type of mouse or other input device.

The present invention system may be a stand-alone system, or may alternatively be connected to or implemented by a network server connected to a network (e.g., LAN, WAN, Internet, etc.) to share and/or distribute information. The network embodiment may utilize a central database for information storage and retrieval, while end-users may remotely access the system via the network.

Patient and examination database 20 keeps track of all the patient demographics and examination information. Example patient demographic information includes patient name, modality type, date of birth, patient identification number, patient physician, etc. Example examination information includes images, drawing, examination date, etc.

Figure 4A:
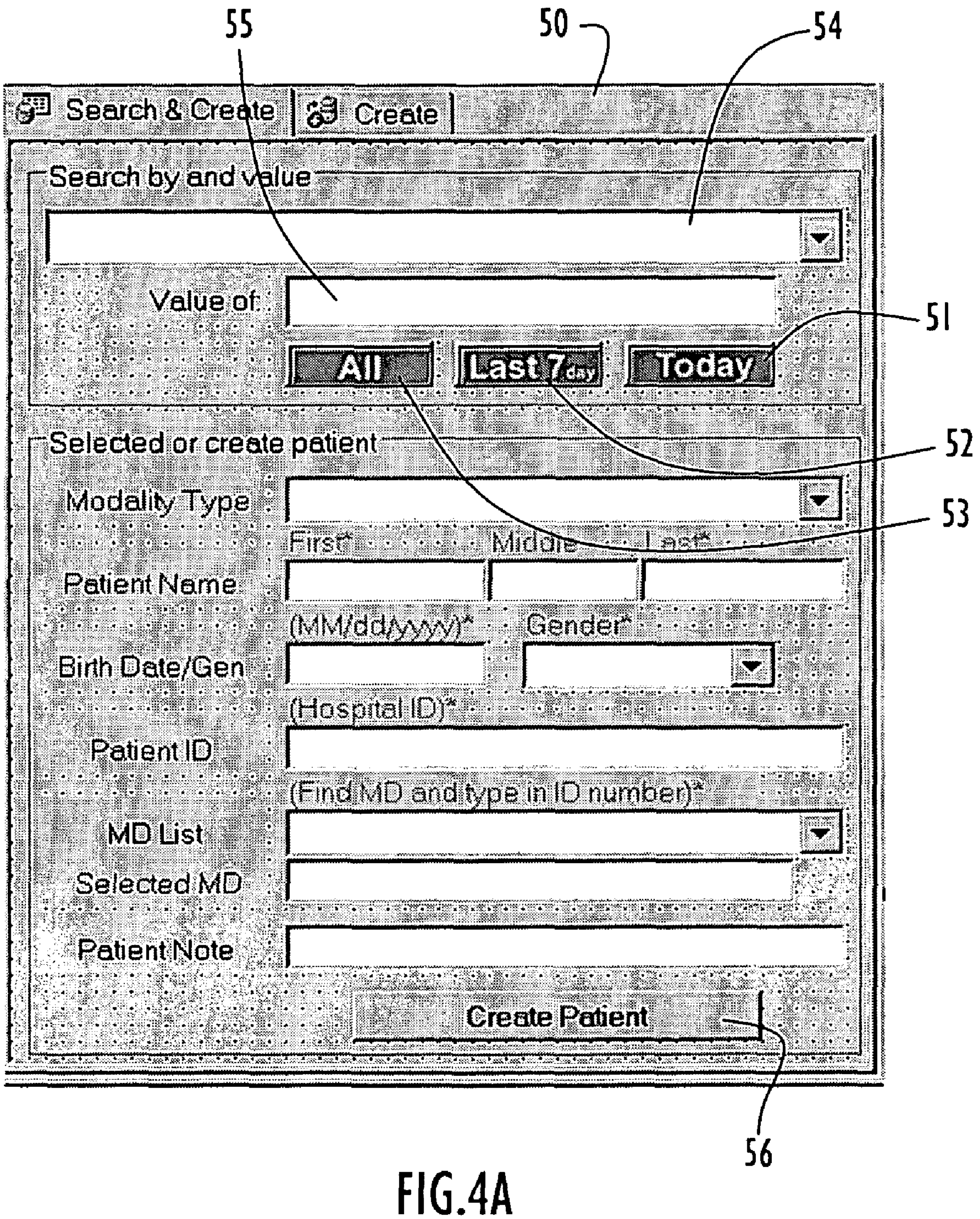
FIG. 4A is a schematic illustration of an exemplary graphical user screen for patient creation and examination search according to the present invention.
Figure 4B:
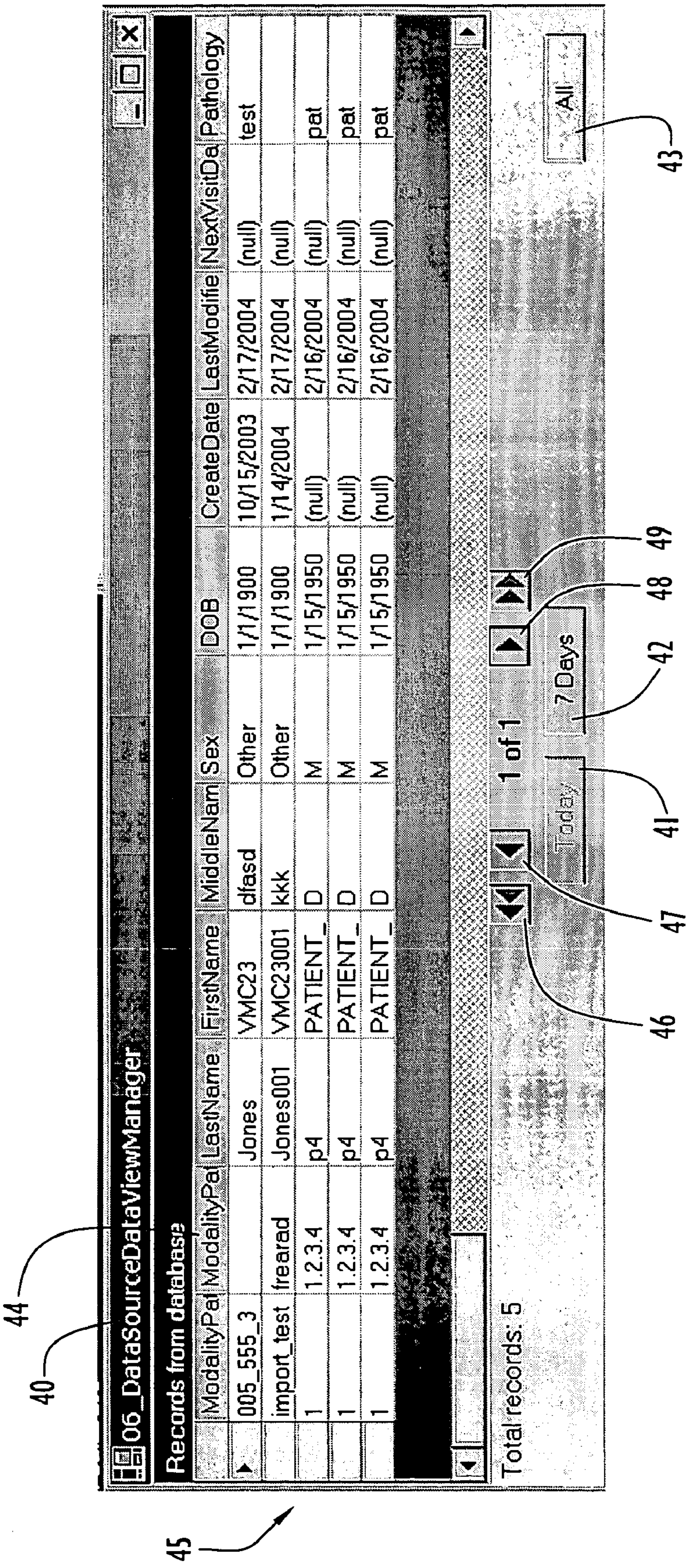
FIG. 4B is a schematic illustration of an exemplary graphical user screen for display and selection of patient examinations according to the present invention.

Patient and exam search module 21 allows the physician to search for existing patients or create new patients. Referring to FIGS. 4A-4B, screens 40, 50 enable an ophthalmologist to search for specific studies. If the desired study is not found, the physician can create a new patient and examination as described below. In particular, a search for examinations may be performed based on date or based on a category and corresponding value. With respect to a date search, screen 50 (FIG. 4A) includes a Today button 51, a Last Seven Day button 52 and an All button 53. Today button 51 enables the system to retrieve all examinations with the current date (or date of system use), while Last Seven Day button 52 retrieves all examinations taken in the last seven days. The All button 53 enables retrieval of all examinations in the system.

A search may further be performed based on a category and corresponding value. Screen 50 further includes a drop-down list 54 containing the various categories and a corresponding field 55 to receive a category value. By way of example only, the categories include: All Patients to display all examinations (e.g., values entered in the corresponding field are ignored); Patient Name (First and/or Last name) to search based on a patient's name using just first name, just last name or both first and last names (e.g., the name does not have to be completely spelled out, where the system searches for the patient's name that contains the field value); Doctor (First and/or Last name) to search based on the doctor's name using just first name, just last name or both first and last names (e.g., the name does not have to be completely spelled out, where the system searches for the doctor's name that contains the field value); Exam Procedure to search based on a procedure type for an examination (e.g. Color, Fluorescein, etc.), where the system searches for the procedure with the exact match; Pathology to search based on the diagnosis of a patient (e.g. Glaucoma, Choroidal Folds, Macular Pucker, etc.), where the system searches for pathology descriptions that contain the field value; Modality Patient ID (Record ID) to search based on a Modality Patient ID generated by a specific capture station or other record generator, where the system searches for the ID that contains the field value; System Patient ID to search based on the system generated system ID for the particular examination, where the system searches for the ID with the exact match; Modality (e.g., MRP, OCT3, TOPCON, IMPORT, etc.) to search based on the modality type used for the examination (e.g. MRP, OCT3, TOPCON, IMPORT, etc.), where the system searches for the modality with the exact match; and Teaching Case Only to search based on the indication of a testing case (e.g., where values entered in the corresponding field are ignored). When a search category and value are entered, date search buttons 51, 52 or 53 are further actuated to perform a search based on category and/or date.

In addition, the physician can search patient and examinations by the various fields within screen 50 (e.g., Patient ID, modality type, patient name, physician name, teaching case only or all patients). The physician enters the desired information or searching criteria within the corresponding fields of screen 50 and actuates one of date search buttons 51, 52 or 53 to initiate the search based on the entered information and/or date.

The system retrieves the appropriate records and displays the retrieved information (e.g., Modality, Patient Name, Gender, Date of Birth, Create Date, Modified Date, Next Visit Date, Pathology, etc.) in a table 45 of screen 40 (FIG. 4B). Patient and exam search module 21 retrieves the desired patient and examination data from either a central database or a stand-alone database. The patient and exam search module preferably utilizes either an Open Database Connectivity (ODBC) or an Object Linking and Embedding Database (OLEDB) connection to the database and employs SQL scripts to search a range of records. Once the desired examination list is displayed, the list or table may be sorted by any item that includes a sort button 44 (e.g., Modality, Last Name, First Name, Sex, Birth Date, Create Date, Modified Date, Pathology, etc.). The sort is alternately performed in descending and ascending order in response to successive button actuations. Screen 40 further includes a Today button 41, a Seven Day button 42 and an All button 43. These buttons are similar to corresponding buttons 51, 52 and 53 described above for screen 50 and enable display of information within table 42 based on date. In particular, Today button 41 displays all examinations with the current date (or date of system use), while Seven Day button 42 displays all examinations taken in the last seven days. The All button 53 enables retrieval of all examinations in the system. Further, a displayed examination may be selected by the physician (e.g., via a mouse, etc.) to enable creation of drawings and reports as described below.

In addition, screen 40 includes buttons or icons to scroll through table 45. In particular, screen 40 includes: a Show Previous Page icon 47 to enable advancement to a previous page of the examination list; a Show Next Page icon 48 to enable advancement to the next page of the examination list; a Show First Page icon 46 to enable advancement to the first page of the examination list; and a Show Last Page icon 49 to enable advancement to the last page of the examination list.

If a search results in no patients being found, a new patient can be created by entering data (e.g., Modality Type, Patient Name, Birth Date, Gender, Patient ID, Selected MD, etc.) in corresponding fields of screen 50 (FIG. 4A) and actuating a create patient button 56. Alternatively, the data may be entered to create a patient without performing a search. The newly created patient information is stored in the patient and examination database, where the patient is further associated with corresponding examinations (e.g., which may be stored in the database prior to or after creation of the patient).

Figure 5:
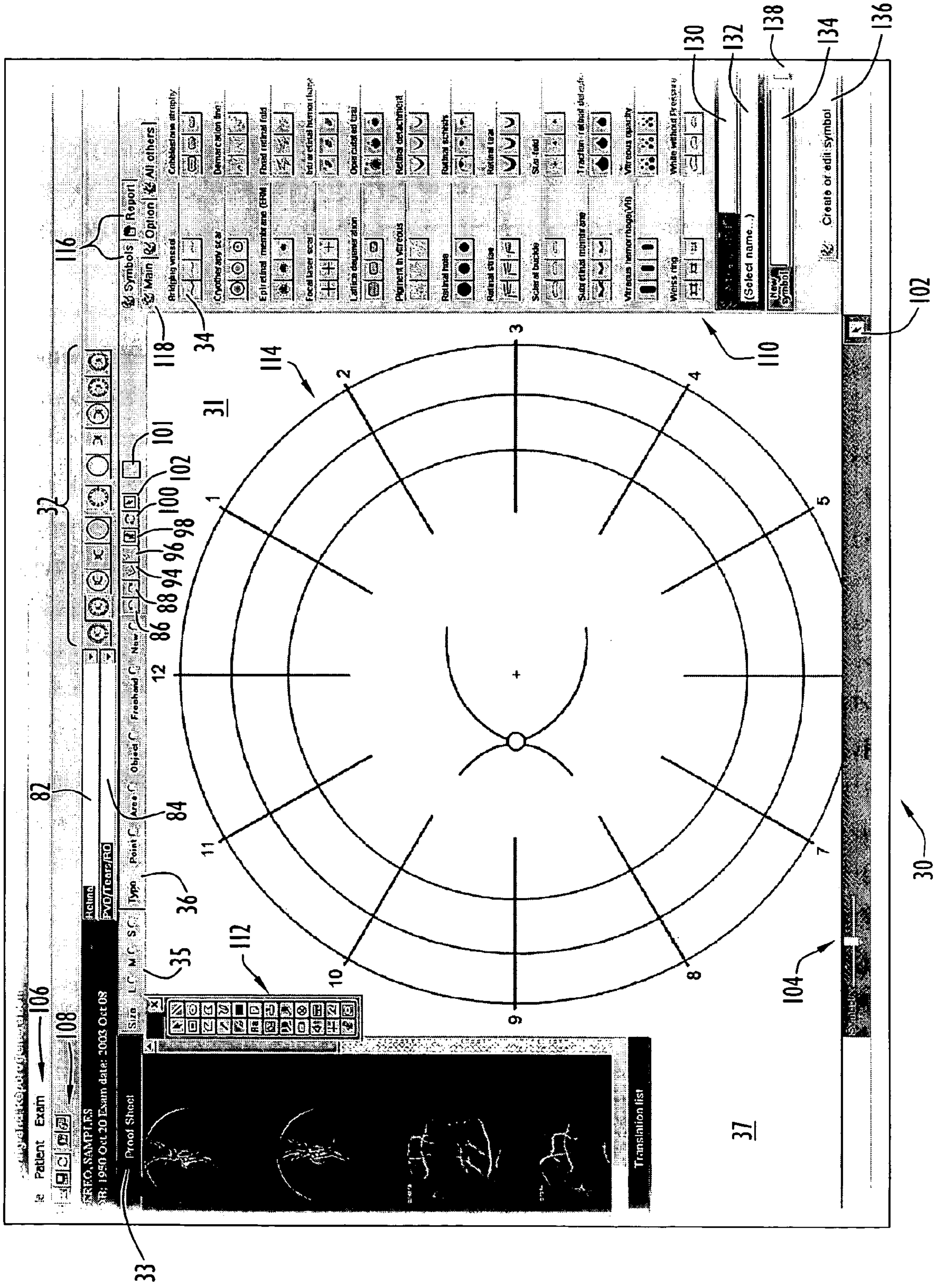
FIG. 5 is a schematic illustration of an exemplary graphical user screen for selection of medical images or templates and drawing on the selected item according to the present invention.
Figure 6:
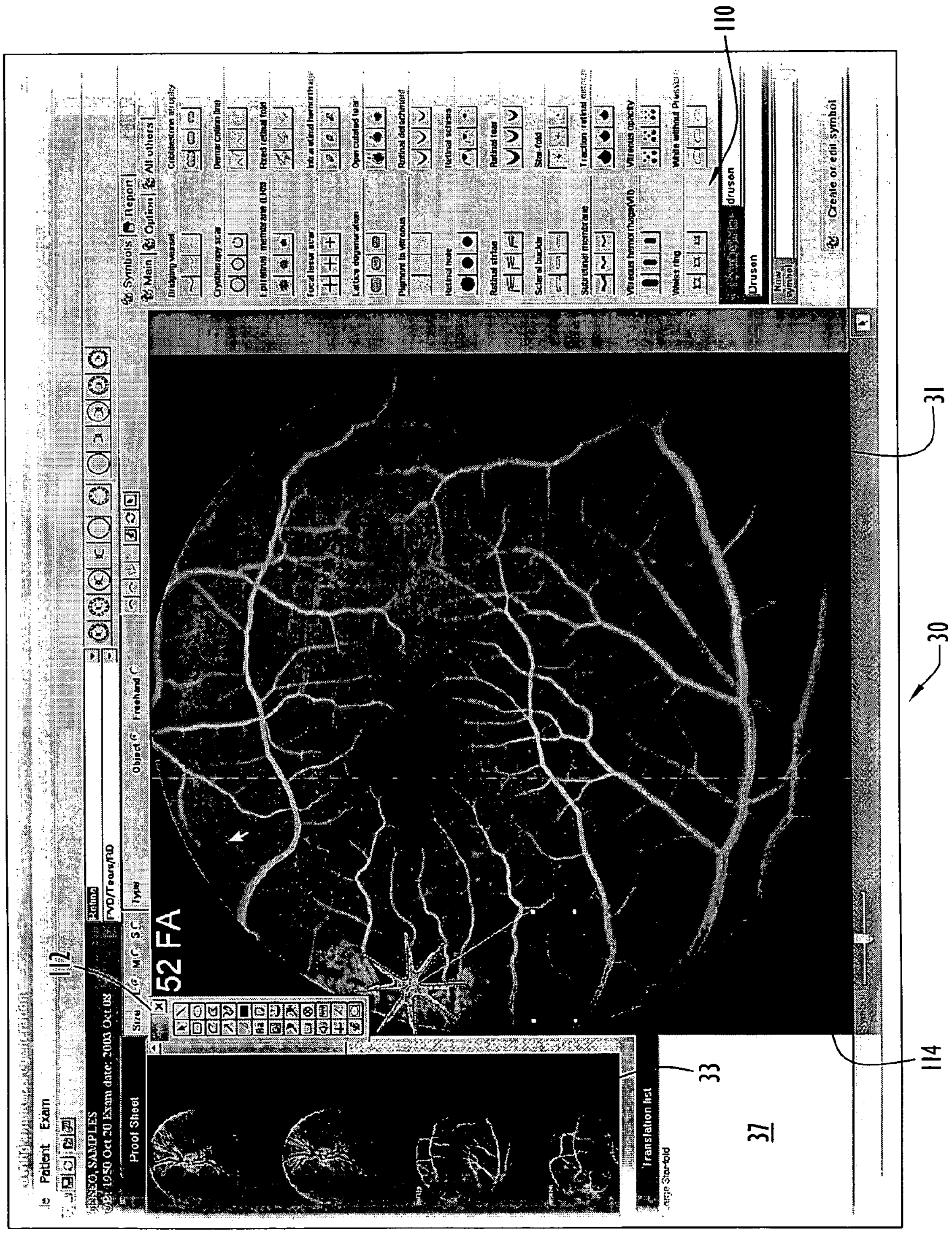
FIG. 6 is a schematic illustration of the graphical user screen of FIG. 5 including a selected image with drawing elements placed thereon by a user according to the present invention.

Once the physician selects (e.g., via a mouse or other input device) one of the examinations displayed in table 45 of screen 40 (FIG. 4B), an interface window is displayed with a proofsheet of images for the selected examination. Referring to FIGS. 5-6, image display module 22 (FIG. 3) displays an interface window 30 including a drawing window or area 31 and a proofsheet window 33 of a selected examination (FIG. 4B). The image display module displays all the medical images associated with the selected examination within proofsheet window 33. The proofsheet window may include scroll features (e.g., arrow and/or sliding bar icons) to be scrolled by a physician in order to display images when the quantity of images exceeds the display area of the proofsheet window. The physician may use one of the images as a background image or template 114 for a drawing (FIG. 6). This background template enables the physician to draw accurate drawings and annotations within drawing area 31. The proofsheet window is preferably disposed on the left hand side of interface window 30 (e.g., as viewed in FIGS. 5-6) and includes large thumbnail medical images associated with the selected examination. These thumbnail images can be scanned by the physician, thereby allowing the physician to rapidly find relevant existing images to use as a reference in the drawing window.

A pre-defined template (FIG. 5) or an image from the proofsheet window (FIG. 6) may be selected (e.g., via a mouse, window buttons or other input devices) and moved to drawing area 31 for utilization as a background image or template 114 for the physician drawing. The selection of a proofsheet image enables the physician to create a drawing and annotations more accurately since physicians refer to the actual medical images of the patient (e.g., from proofsheet window 33) to draw or place identifiers. Thus, physicians create accurate drawings since the exact location of a disease may be determined from and identified on actual medical images.

The resulting physician drawing (e.g., physician modifications to the background image) is saved as a separate drawing or annotation file (e.g., without the original background image) within database 20 (FIG. 3). This separate drawing file is associated with the background image (or background image file), where the annotation file can be reloaded or overlaid with the appropriate background image to reproduce the physician drawing at a later time for viewing and/or editing. Thus, a physician may update drawings over time in accordance with patient conditions. Image display module 22 generates an image location URL or other identifier for the files (e.g., background image and/or annotation files) based on uniquely identifiable database information (e.g., patient name, date of birth, exam date, patient ID, etc.).

If the physician selects one of the images in proofsheet window 33 (e.g., via a single or double click of a mouse or other input device), a Proview type image viewer appears to display the selected image and provide various image manipulation tools (e.g., zoom in/out, magnification, rotation, measurement, brightness and contrast control, etc.) in substantially the same manner disclosed in the aforementioned patent applications. When the physician double clicks an image from proofsheet window 33, interface window 30 is updated with the selected image for use as the background template to enable the physician to draw very accurate drawings as described below. If the physician selects an image from proofsheet window 33, the size of the selected image is adjusted to fit into the drawing area. When the patient does not have examination data, interface window 30 is basically empty.

In the case of a personal computer (PC) application, proofsheet window 33 can be hidden or shown based on the physicians preference in order to provide more space for the drawing and enable display of a symbol window 110 including various selections of predefined drawing elements or symbols. The symbol window is preferably disposed on the right side of interface window 30 (e.g., as viewed in FIGS. 5-6). This option is configurable from a system preference menu to either show or hide the proofsheet window. Thus, the proofsheet window is displayed in accordance with the type of PC employed by the physician.

Drawing and annotation module 25 (FIG. 3) allows the physician to select various types of background images (e.g., from proofsheet 33 (FIG. 6), predefined image templates (FIG. 5)) and predefined symbols 34 to rapidly create a drawing in drawing window 31. This module basically enables generation of physician drawings and displays proper annotations for those drawings. The physician may select a background image or template 114 for a drawing and continue to change the background image and provide drawings overlaid with the selected image. The resulting drawings are overlaid over time and saved to one annotation file for future reference as described above. Saved annotation files should be unique for each examination and medical image, if the image is used as a background image.

Interface window 30 initiates drawing based on selection of background images (e.g., via a mouse or other input device). In order to commence drawing, the physician must select a background image from proofsheet 33 or via template buttons 32 disposed toward the top of interface window 30. The template buttons each correspond to a particular template. FIG. 5 shows an exemplary predefined template serving as background image 114. By way of example only, image templates for the Opthalmology area include Retina, External/Lids, Anterior segment, Lens, Gonioscopic examination, Macula, Peripheral retina and ROP, where the templates corresponding to template buttons 32 include templates for Center Circle, DET circle, OD, ODDet, OD center, OS, OSDet, OS center, Anterior and Exterior. The physician may select a template via template buttons 32 or an area drop down list 82 as described below. The system displays appropriate predefined symbols for selection and drawing on the selected template as described below. However, interface window 30 may employ any quantity of any suitable types of templates and corresponding buttons.

Once the background image is selected and drawing area 31 includes the selected image, the physician starts to draw and annotate on the selected image within drawing area 31. The drawings, templates, symbols and annotations enable the physician to identify the type and location of various diseases or other eye related matters on the background image. The physician may select multiple background images over time. In this case, the system displays multiple images in drawing area 31 as an overlay pattern. With template buttons 32, the physician can change the background image to draw different types of drawings. Previously drawn objects remain on drawing area or window 31 even though a new background image has been selected and displayed.

The type of symbol drawn can be selected by type radio buttons 36 disposed toward the top of interface window 30. The types of symbol buttons include: (1) Point: symbol that just needs to be dropped by a single mouse click; (2) Area: the physician needs to drag and drop or draw an area and close, where the symbol is then used to fill the area as a pattern; (3) Object: predefined drawing pattern and/or symbol, where the physician can resize this object; (4) Freehand: the physician can draw any shape by freehand drawing, where the shape will remain open and the pattern/color is associated only with the freehand drawn line; and (5) New: an area object with new user defined characteristics (e.g., color, shape etc.). Each symbol is of one of the types described above. However, the physician can select different types of drawing methods for symbols of the same type.

Figure 22:
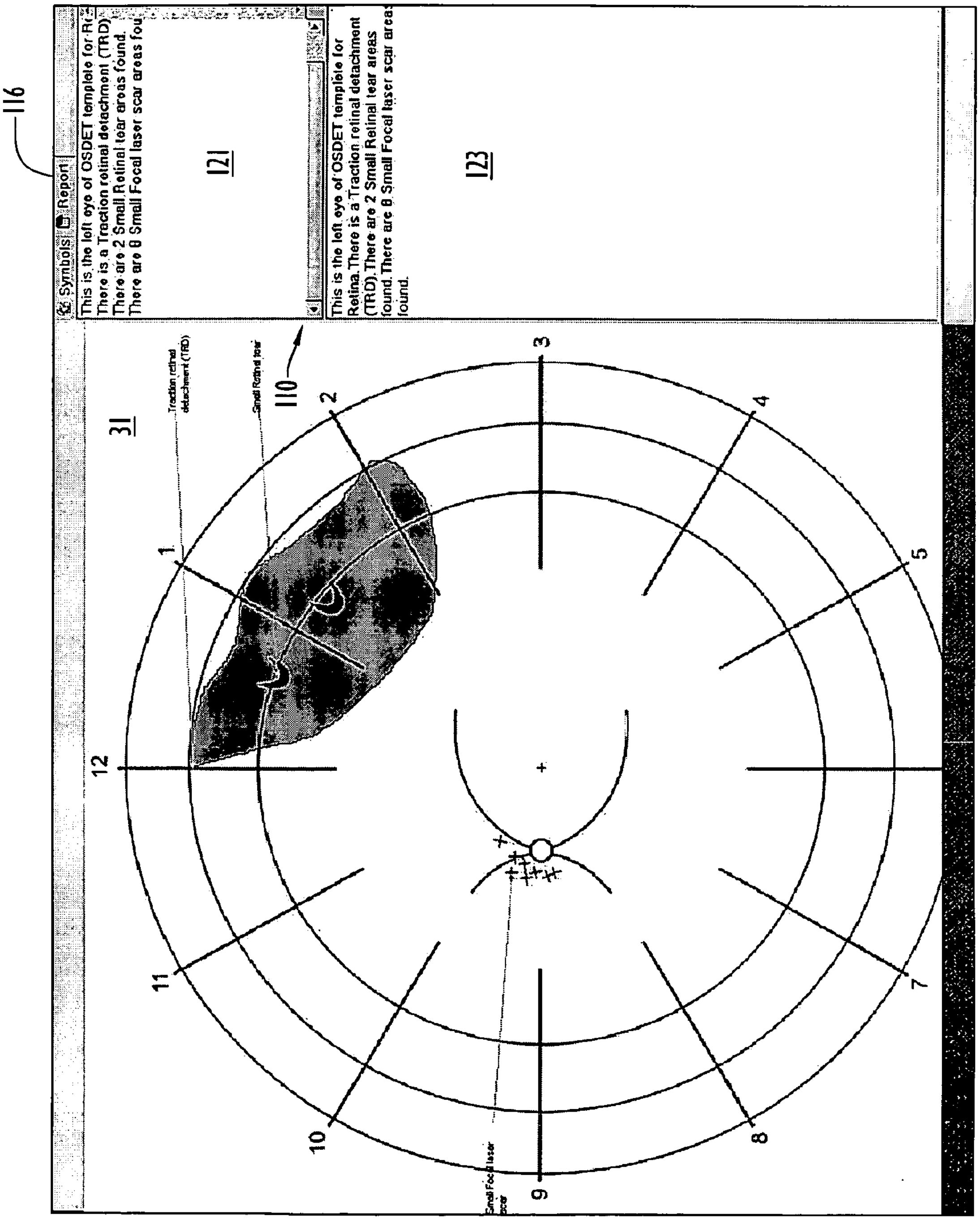
FIG. 22 is a schematic illustration of an exemplary graphical user screen for drawing on a selected background image and including a report window with textual descriptions of the drawing according to the present invention.

Most necessary drawing symbols are predefined to save time. The system provides the physician ease of use and convenience for drawing and annotation. Accordingly, symbol and report window 110 is disposed toward the right side of interface window 30 (e.g., as viewed in FIGS. 5-6). Symbol window 110 includes a series of tabs 116 each associated with a corresponding function. The tabs are associated with symbol management and report functions as described below. The report tab displays areas with a textual description of findings in the background template. Referring to FIG. 22, the report tab displays a scrollable area 121 and a report window 123 each containing a textual description of the drawing symbols on the background image. The textual description is generated by auto translation module 26 (FIG. 3) as described below. This textual description is combined with an XML based report template to produce customized reports (e.g., referral letters, clinical notes, etc.) as described below.

Figure 8:
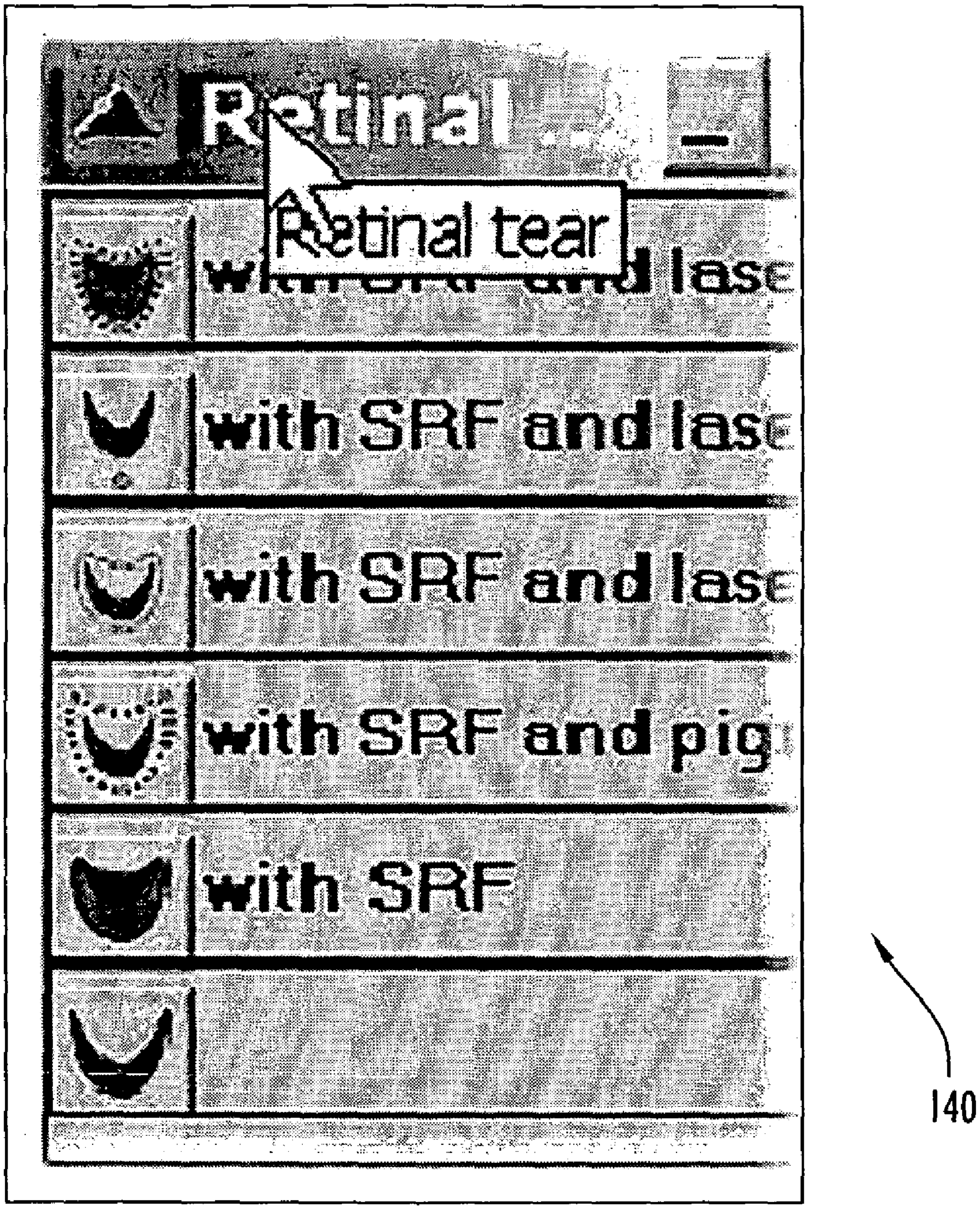
FIG. 8 is a schematic illustration of an exemplary graphical user screen displaying modifier elements for a predefined drawing element according to the present invention.

The symbol tab provides symbol choices, thereby obviating the need for the physician to draw a detail shape of the drawing. A series of sub tabs 118 are displayed in response to actuation of the symbol tab. Each sub tab 118 is related to a particular symbol category (e.g., main, option and others) and includes one or more symbols for placement on the background template. The window may further include tabs for the most recently used and the most frequently used symbols for each disease or problematic area. By way of example, the main sub tab (FIGS. 5-6) includes a plurality of symbols arranged or grouped into diseases or problematic areas. Each group includes a series of symbols each of a different size. In order to enable the physician to rapidly indicate a combination of conditions, predefined symbols 34 within window 110 may be associated with modifiers to enable selection and placement of a combination of identifiers. An exemplary modifier list associated with a predefined symbol for a retinal tear is illustrated in FIG. 8. Modifier list 140 includes various further conditions (e.g., retinal tear with SRF, etc.) and associated symbols for placement on the background template. Modifiers for a symbol may further be employed to indicate negative medical findings (e.g., to indicate a certain area does not contain a particular problem, such as a retinal tear). The other symbol sub tabs 118 may be arranged in a similar fashion, where the options sub tab includes less frequently used symbols, while the others sub tab shows all the symbols for the selected category.

The symbols of window 110 are changed automatically in response to the background image selection in order to assist the physician to draw in drawing area 31. The symbols may further be automatically changed in response to the physician indicating the area and type of disease or problem. In particular, interface window 30 includes area and abnormality drop down lists 82, 84 disposed toward the top of that window. List 82 includes selections for various areas of the eye, thereby indicating the type of template for the background image. List 84 includes selections for the abnormalities or diseases associated with the selected area or template. The physician may utilize the lists to indicate the desired area and abnormalities, where the system provides the corresponding symbols for the selected items in symbol window 110. The automatic change of symbols enables the physician to save drawing time and eases use of the system. The physician may also change the window functions by selecting a different tab 116, 118 in window 110. Further, when the physician selects one of the symbols from window 110, the system detects the type of category of that symbol in order to display proper symbol type (e.g., Point, Area, Object, Freehand or New). Once the system detects the symbol type of the selected symbol, the system shows the proper type of the selected symbol. For example, if the physician selects retina tear that belongs to each of the area, object and freehand categories, the system hides the radio button associated with the remaining categories (e.g., point and new).

The symbols from window 110 are transferred to drawing area 31 via a click or drag and drop operation. The symbols may represent positive or negative medical findings. In particular, interface window 30 includes select mode icons 102 each disposed toward a respective top and bottom portion of window 30. The icon toggles the window between a selection mode and an insert mode. Selection mode enables the physician to select a predefined symbol from symbol window 110. The physician may utilize a mouse or other input device to select a symbol from those within symbol sub tabs 118.

Alternatively, a physician may search for a desired symbol based on a textual description. Specifically, symbol window 110 includes search field 130 and symbol drop down list 132 disposed toward the bottom of symbol window 110. The physician enters a textual description of the desired symbol in search field 130 and the system searches the symbols for a partial match. Search results are displayed in symbol drop down list 132, where the physician may select a desired symbol via the mouse or other input device.

Figure 7:
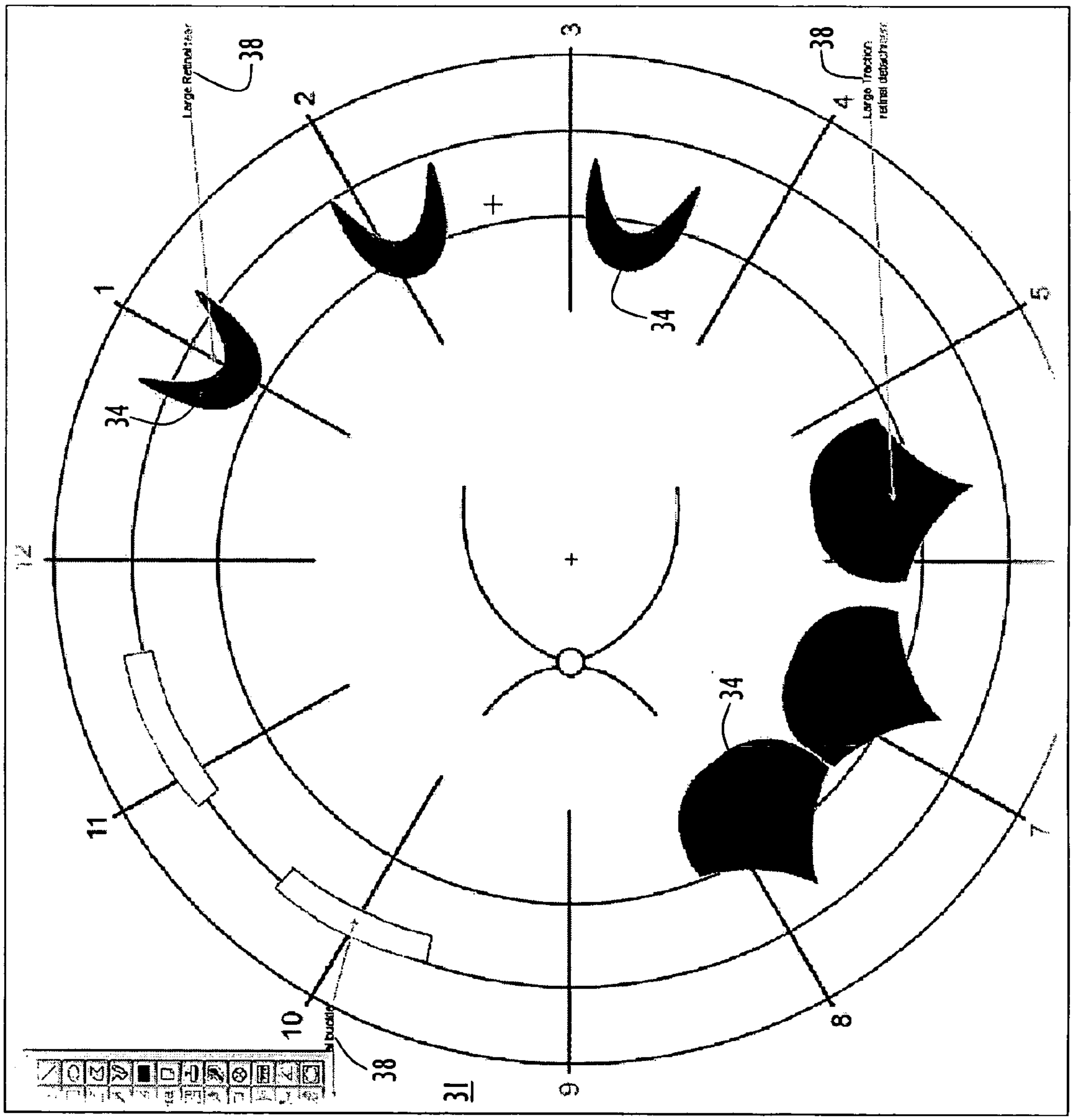
FIG. 7 is a schematic illustration of a portion of the graphical user screen of FIG. 5 including a template with drawing elements placed thereon and automatically generated corresponding annotations according to the present invention.

Once a predefined symbol is selected (e.g., via selection from a sub tab or via a search), actuating an icon 102 enables the physician to insert the selected symbol on background template 114. A symbol may be selected once, while subsequent actuation of a mouse or other input device in insert mode places one or more selected symbols at desired locations on the background template. The system automatically orients each inserted symbol along a radial axis extending from the center of the background template to the location of the object within that template. For example, FIG. 7 illustrates predefined symbols 34 disposed on background template 114 and oriented toward the template center. The system may be designed for a Tablet PC, where a user can use a pen based drawing on the LCD screen of the Tablet PC. Pen and ink inputs from the screen are submitted to the system and converted to an input event to enable updating of the screen.

Figure 9:
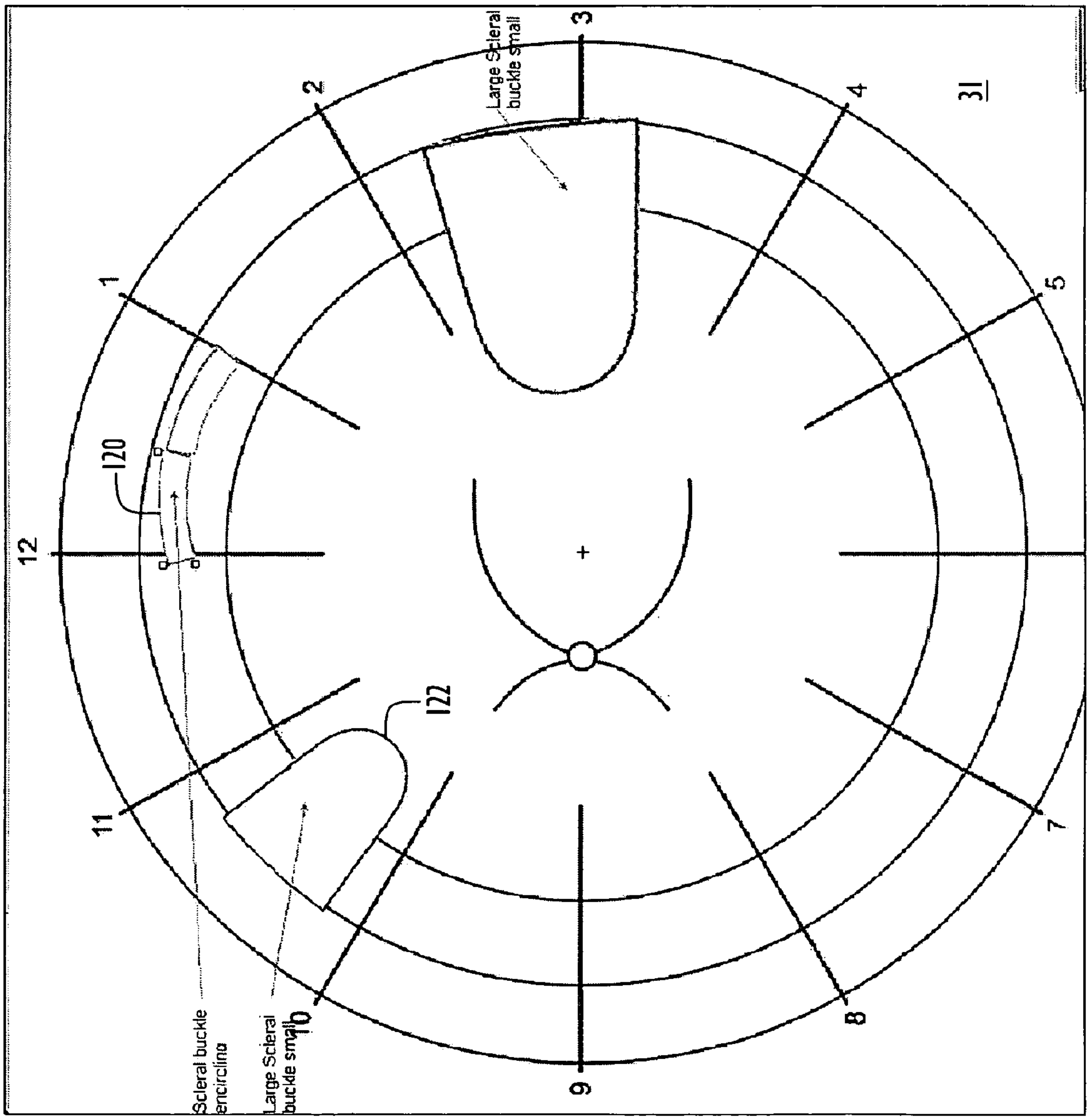
FIG. 9 is a schematic illustration of a portion of the graphical user screen of FIG. 5 including a template with drawing elements drawn thereon in response to user specifications according to the present invention.
Figure 10:
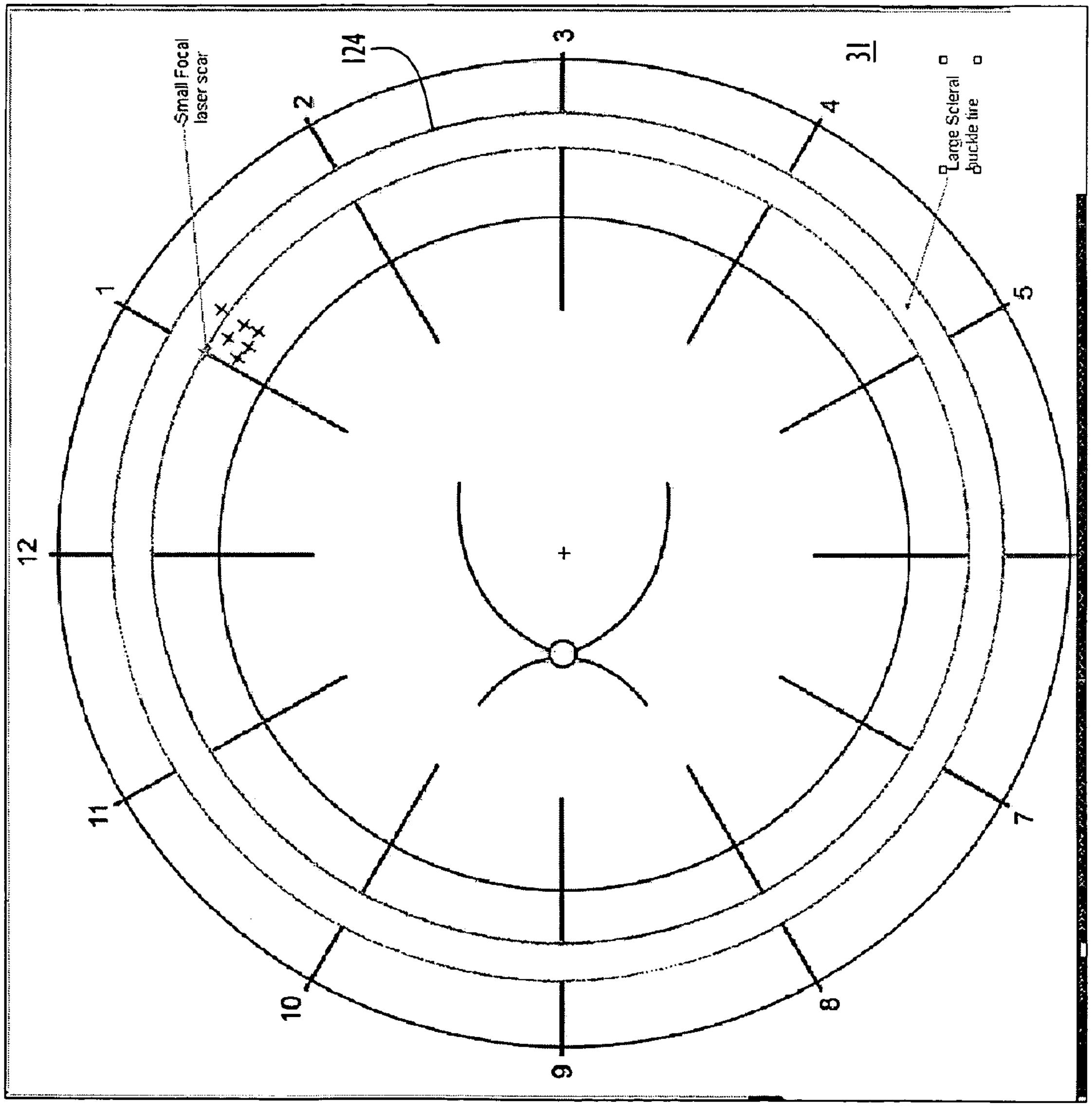
FIG. 10 is a schematic illustration of a portion of the graphical user screen of FIG. 5 including a template with an alternative drawing element drawn thereon according to the present invention.

Some predefined symbols may be drawn by the system in response to location points indicated by the physician. For example, a scleral buckle symbol (FIGS. 5-6) may be drawn by the system in response to user specified locations. This type of symbol represents objects placed in the eye to enhance focus and typically includes modifiers as described above to provide selection of a scaling arc, a radial arc or an encircling element. The particular symbol is selected via an icon 102 as described above. With respect to a scaling arc, the user indicates the endpoints of the arc on the background template and the system draws an arc between the specified points. An exemplary scaling arc 120 is illustrated in FIG. 9. A user specifies end-points along a radial axis of the background template and the system draws a closed arc extending the radial distance between the specified points. Exemplary radial arcs 122 are illustrated in FIG. 9. An encircling element is in the form of a ring, where the system places the ring on the background image at a predetermined location. The user may alter the position by adjusting the size of the symbol as described below. An exemplary encircling element 124 is illustrated in FIG. 10. The system automatically orients the scaling and radial arcs toward the template center as described above.

The default size of a predefined symbol for a drawing is configurable based on the preference setting at system installation. When the system is installed for the first time, the default symbol size is medium. However, the physician can select different sizes for the symbol to enable placement of a properly sized symbol without resizing that symbol. The system provides predefined symbol sizes to save the physician time. The predefined sizes are covered in most cases, however, the physician may change the symbol size as described below. By way of example only, the predefined symbol sizes include small (S) (e.g., 50×50 pixels), medium (M) (e.g., 100×100 pixels) and large (L) (e.g., 200×200 pixels). However, the system may utilize any quantity of predefined symbol sizes of any desired dimensions.

The size of predefined symbols 34 can be adjusted by size buttons 35 (e.g., 'L' for large, 'M' for medium and 'S' for small) disposed toward the top of interface window 30. Alternatively, interface window 30 further includes a size bar 104 disposed toward the bottom portion of the window. The size bar includes a sliding bar to adjust the size of a selected symbol placed on background template 114.

In the event the default setup symbol size is small and the physician selected one of the symbols, the system displays the small size of the symbol on the drawing area. The physician can change the size of the symbol while the drawn symbol is still active on the window by selecting a different symbol size via buttons 35 or size bar 104. Alternatively, the physician may utilize a keyboard to indicate the symbol sizes. For example, the physician may depress the 'S' key for small, 'M' key for medium and key for large. This enables the physician to change the symbol size very easily without clicking other buttons.

Figure 11:
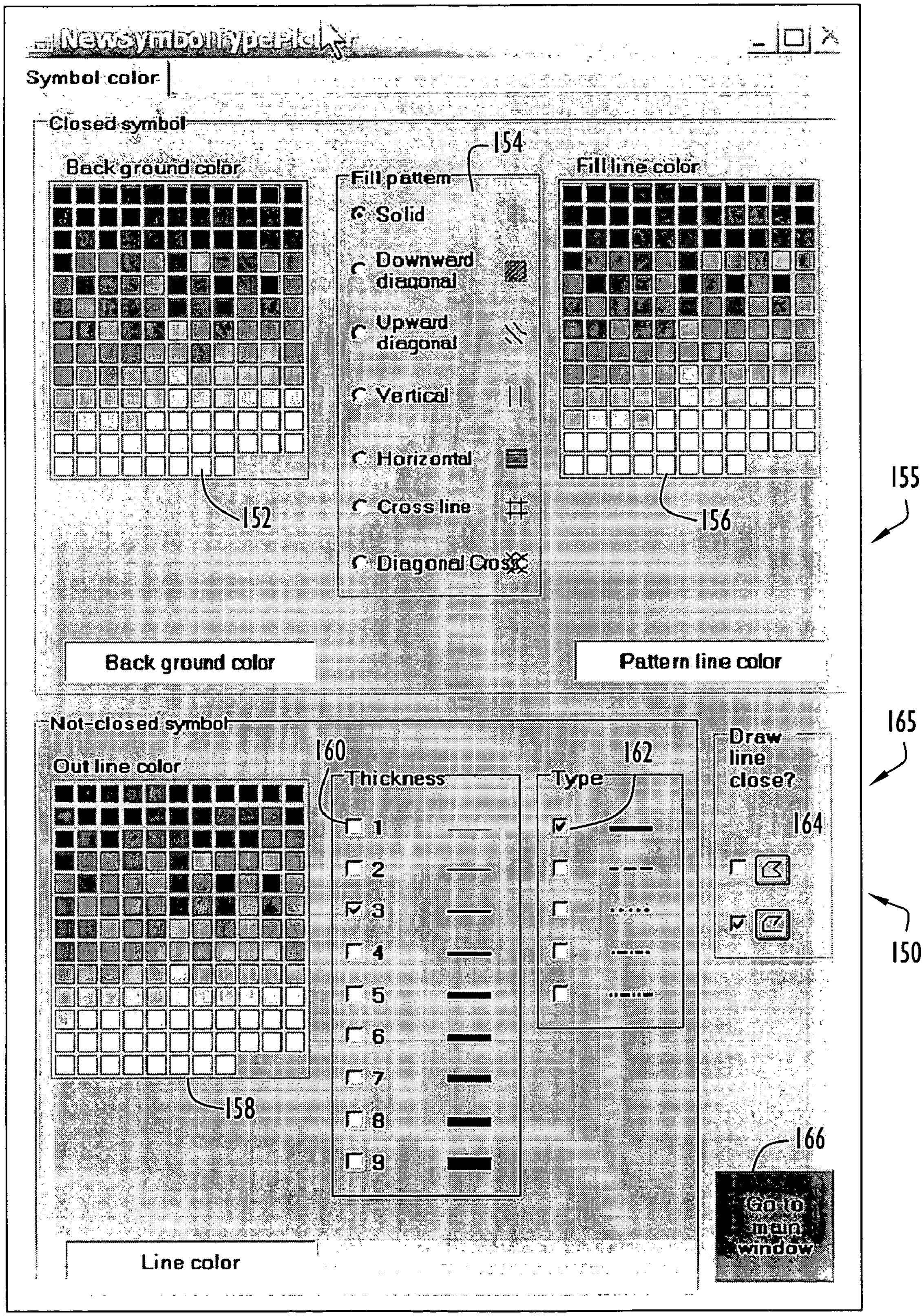
FIG. 11 is a schematic illustration of an exemplary graphical user screen to define and/or edit a drawing element according to the present invention.

Basically, the types of pre-defined symbols employed by the system include Main symbols, Option symbols and All other symbols as described above (FIG. 5). A user may further create or edit symbols by actuating or clicking a create button 136 on interface window 30. Drawing module 25 includes a symbol editor module 80 (FIG. 17) and a symbol store or farm 76 to manage symbol editing and/or creation. A separate window appears to enable a user to edit and/or create a symbol for a selected symbol category. For example, if the user selects Retina tear and clicks the edit symbol button, the symbol window appears to create or edit a Retina tear symbol. In particular, symbol window 110 includes a new symbol field 134 disposed below drop down list 132. The physician selects the appropriate symbol sub tab 118, enters the name of the new symbol in new symbol field 134 and actuates create symbol button 136 to define a new symbol. The physician may alternatively actuate define icon 138 disposed adjacent field 134 to define the symbol. The system displays symbol editor window 150 to define the symbol properties as illustrated in FIG. 11. Window 150 includes sections 155, 165 to respectively define closed and open type symbols. A closed symbol generally refers to a symbol defining a closed or bounded area, while an open symbol includes an open portion or area (e.g., parabola, etc.). The type of symbol may be indicated via type radio buttons 164 disposed within open section 165. These buttons may be actuated by the physician to indicate the symbol type, or may be automatically controlled by the system to indicate the symbol type in accordance with the window section (e.g., closed or open) receiving input.

Closed symbol section 155 includes a background color palette 152, fill pattern radio buttons 154 and a fill color palette 156. The background color palette enables selection of the color of the new symbol (e.g., outline and interior), while fill pattern buttons enable selection of the pattern (e.g., solid, downward diagonal, upward diagonal, vertical, horizontal, cross line, diagonal cross, etc.) to be disposed within the new symbol. The fill color palette enables selection of the color of the lines for the selected fill pattern.

Open symbol section 165 includes an outline color palette 158, thickness radio buttons 160 and type radio buttons 162. The outline color palette enables selection of the color of the lines defining the new symbol (e.g., outline), while the thickness and type buttons enable selection of the thickness and pattern for those lines (e.g., solid lines, dashes, dashes and dot patterns, etc.).

Figure 12:
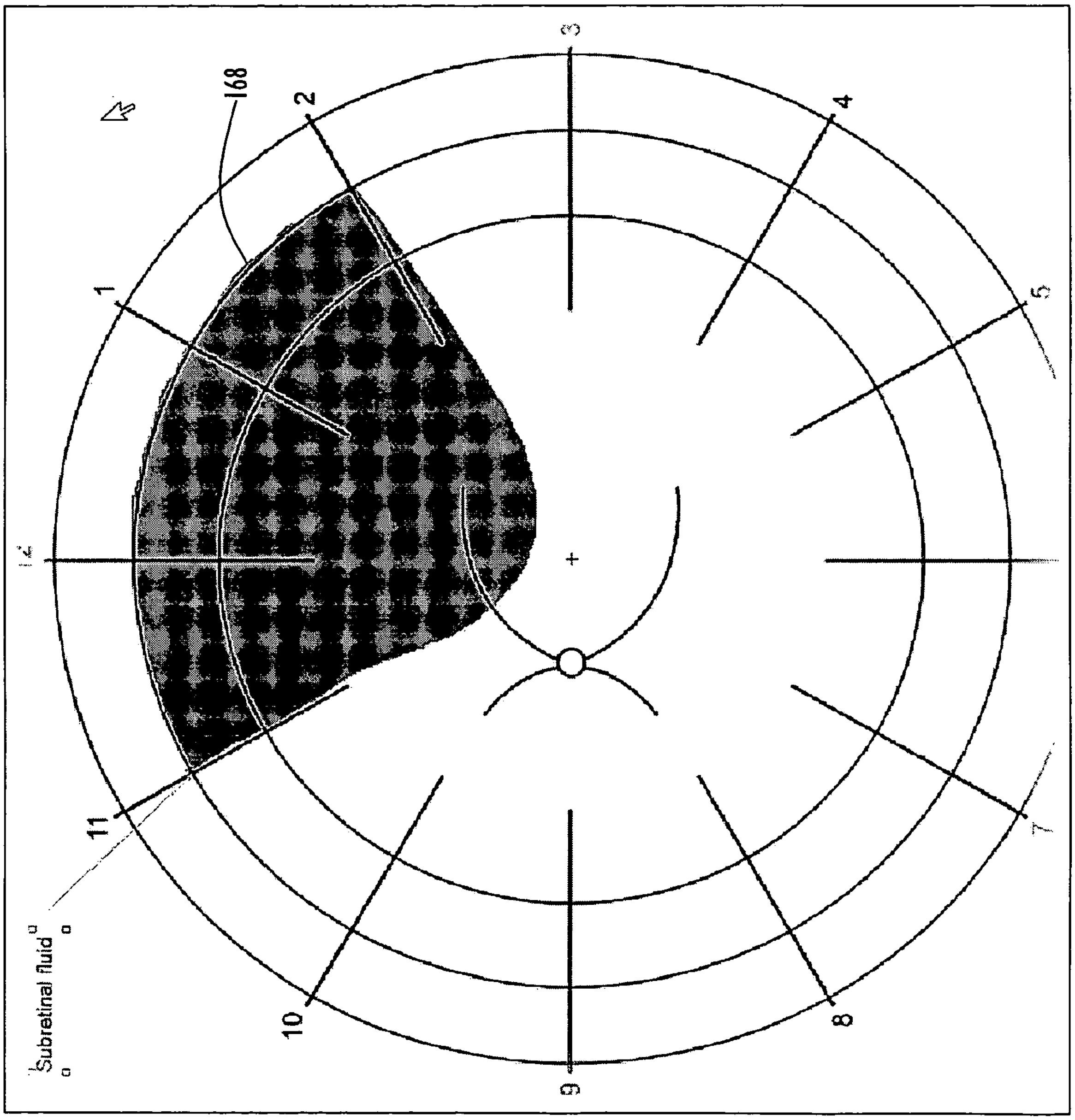
FIG. 12 is a schematic illustration of a portion of the graphical user screen of FIG. 5 including a template with a drawing element placed thereon by a user, where the system closes the open drawing element via generation of an arc according to the present invention.

Once the desired type and properties have been selected, the physician actuates window button 166 to display interface window 30 (FIG. 5). The physician may draw the desired symbol within drawing area 31 via a mouse or other input device, where the system provides the various properties (e.g., line thickness, line type, background, fill and outline colors, etc.) according to the physician selections in symbol editor window 150. Open type symbols remain in an open state after completion by the physician. However, if the new symbol type is closed, the system completes any open portions remaining in the physician drawing of the new symbol. This may be accomplished by connecting the open portions with a linear or straight line between open portion end-points. Alternatively, the system may close the open portions with an arc between the open portion end-points. An exemplary closed symbol with an arc provided by the system to connect open portion end-points is illustrated in FIG. 12. Specifically, an arc 168 is provided by the system along the intermediate radial ring (e.g., the arc extends along the ring between eleven o'clock and two o'clock) to close the drawn symbol. The physician may further indicate the object type via buttons 36 as described above. The system stores the new symbol in symbol farm 76. After the symbol is saved, the symbol becomes one of the symbols for the selected category and is added to the appropriate window or sub tab 118 as an additional selection for future use.

With respect to editing, the physician may select a predefined symbol (e.g., via mouse or other input device selection and an icon 102, via a search, etc.) as described above and actuate create button 136. The system displays symbol editor window 150 to enable modification of the symbol properties and/or drawing of the symbol in substantially the same manner described above. The symbol creation and editing feature allows users to create their own style of symbols and to add symbols to a symbol list for re-using symbols over time, thereby obviating the need to re-create the symbols. The symbol list typically expands over time to enable the user to build their own style of drawing symbols for added convenience.

The physician may further add various objects (e.g., lines, text, color, etc.) on the background image within drawing area 31. A basic drawing tool 112 is disposed toward the left top corner of the drawing area (e.g., as viewed in FIGS. 5-6). The drawing tool includes a plurality of icons or buttons each providing a corresponding drawing function similar to those within conventional painting applications. For example, the drawing tool may include functions to draw various shapes, insert text, delete or erase portions of the drawing, measure drawing portions, etc. The drawing tool is typically displayed upon entry into interface window 30, where display of tool 112 may be toggled via display tool button 98 disposed toward the top of interface window 30. A pen or conventional mouse may be utilized to draw a line, point, object and/or area symbols in the drawing window. This basic drawing tool only annotates the drawing and does not in any way affect the textual reports.

By way of example, Table I below provides the most common symbols or items used for retinal drawings of the peripheral retina. The symbols may be placed on the screen in various manners as described above. For example, symbols may be commonly utilized in a 'point' fashion, where a single item is placed for each actuation of an input device (e.g. mouse drag and drop, the pen tip touches the screen, etc.). Further, some symbols may be in the form of enclosed areas (or closed symbols) delineated by outlining the area on the screen (e.g., via mouse clicks, the pen tracing the outline, etc.). Other symbols may be grab-and-drop items, where the symbol is disposed in a specific location within the drawing background image (e.g., via mouse, pen, etc.). A freehand drawing option is typically available for a majority of the symbols (e.g., where the mouse or pen is used on the screen just like a pen on paper allowing any shape to be drawn). The physician is preferably provided with drawing method options to employ, where the most common method is typically set as the default.

TABLE I

| Symbol | Type |
| --- | --- |
| Retinal tear | object, freehand |
| Operculated tear | object, freehand |
| Retinal hole | object, freehand |
| Lattice degeneration | area, freehand |
| Retinal detachment | area, freehand |
| Retinal schisis | area, freehand |
| Outer layer hole | object, freehand |
| Inner layer hole | object, freehand |
| Demarcation line | freehand |
| Cystic retinal tuft | object, freehand |
| Meridonal fold | object, freehand |
| Enclosed ora bay | object, freehand |
| Cobblestone atrophy | area, freehand |
| Peripheral cystic retinal degeneration | area, freehand |
| Preretinal opacities | freehand |
| Retinal dialysis | area, freehand |
| Giant retinal tear | object, freehand |
| Star-fold | object, freehand |
| Epiretinal membrane | freehand |
| Subretinal membrane | freehand |
| Pigment in vitreous | point, freehand |
| Intraretinal hemorrhage | point, freehand |
| Preretinal hemorrhage | freehand |
| Weiss ring | object |
| Laser scar | object |
| Cryo scar | object, area, freehand |
| Traction retinal detachment | area, freehand |
| Vitreous hemorrhage | freehand |

By way of example only, Table II below provides the most common symbols used for retinal drawings in diabetic retinopathy. The symbols may be placed on the screen in various manners as described above.

TABLE II

| Symbol | Type |
| --- | --- |
| Intraretinal hemorrhage | point, freehand |
| Exudate | point, freehand |
| Microanuerysm | point |
| Venous beading | freehand |
| Retinal edema | area, freehand |
| Cotton-wool spot | point, freehand |
| Focal laser scar | point |
| Panretinal laser scar | point, object (sector, hemi-field, full-field) |
| Retinal neovascularization | freehand |
| Disk neovascularization | freehand |
| Fibrovascular proliferation | freehand |
| Traction retinal detachment | area, freehand |
| Retinal striae | freehand |
| Vitreous hemorrhage | area, freehand |
| Pre-retinal hemorrhage | area, freehand |
| Sub-hyaloid hemorrhage | area, freehand |
| Epiretinal membrane | freehand |

Once a symbol is placed in drawing area 31, the symbol can be resized as described above. Further, the selected symbol may be rotated according to physician preference. Interface window 30 includes rotation icons 86, 88 disposed toward the top of the window. Icon 86 enables rotation of a selected symbol in a counter-clockwise direction, while clockwise rotation of the selected symbol occurs in response to actuation of icon 88. Each actuation of icons 86, 88 rotates the symbol a predetermined quantity of degrees in the corresponding direction, where the amount of rotation for each actuation may be set to any desired value.

Figure 13:
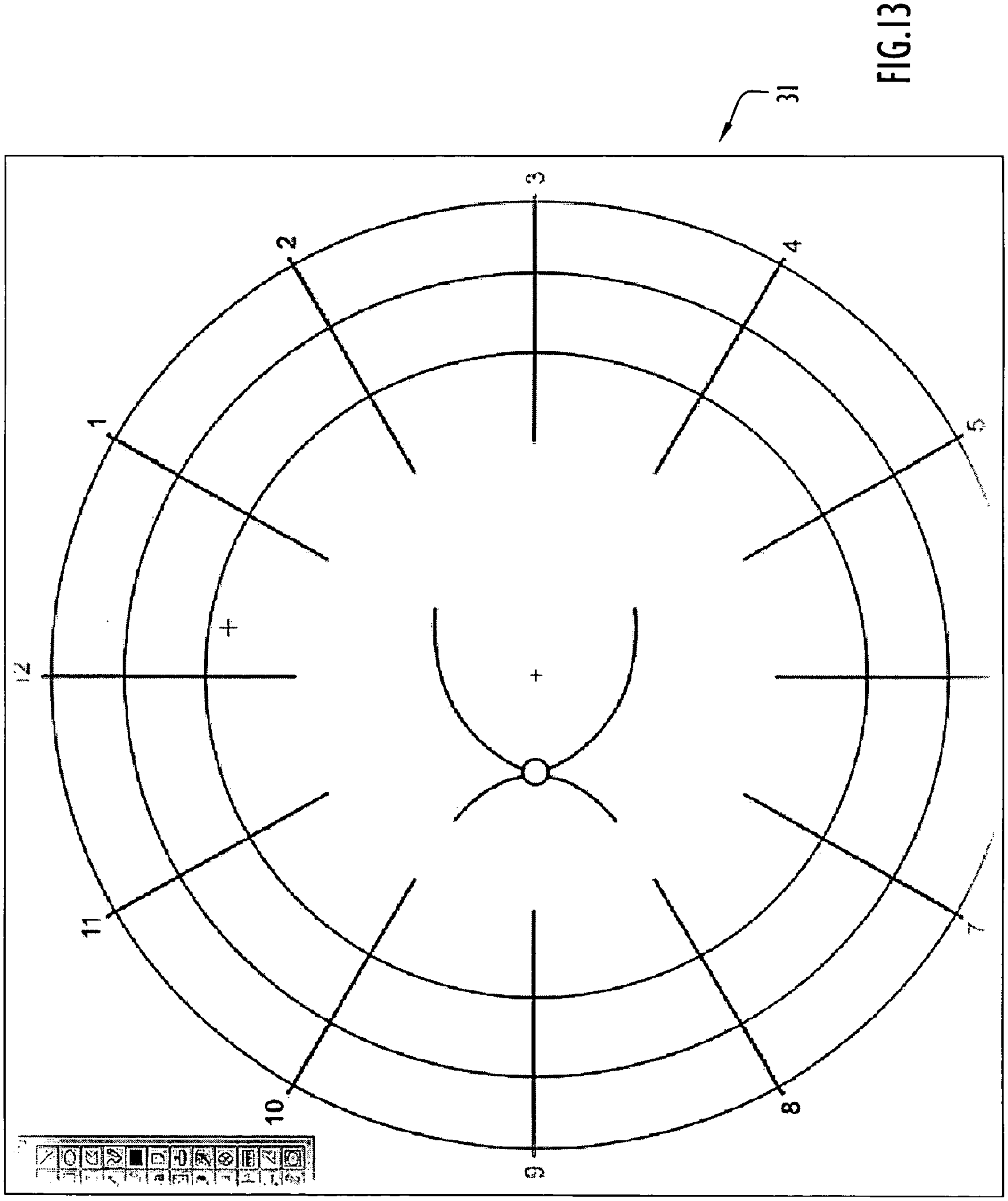
FIG. 13 is a schematic illustration of a template within the graphical user screen of FIG. 5 subsequent a user applying a zoom feature according to the present invention.
Figure 14:
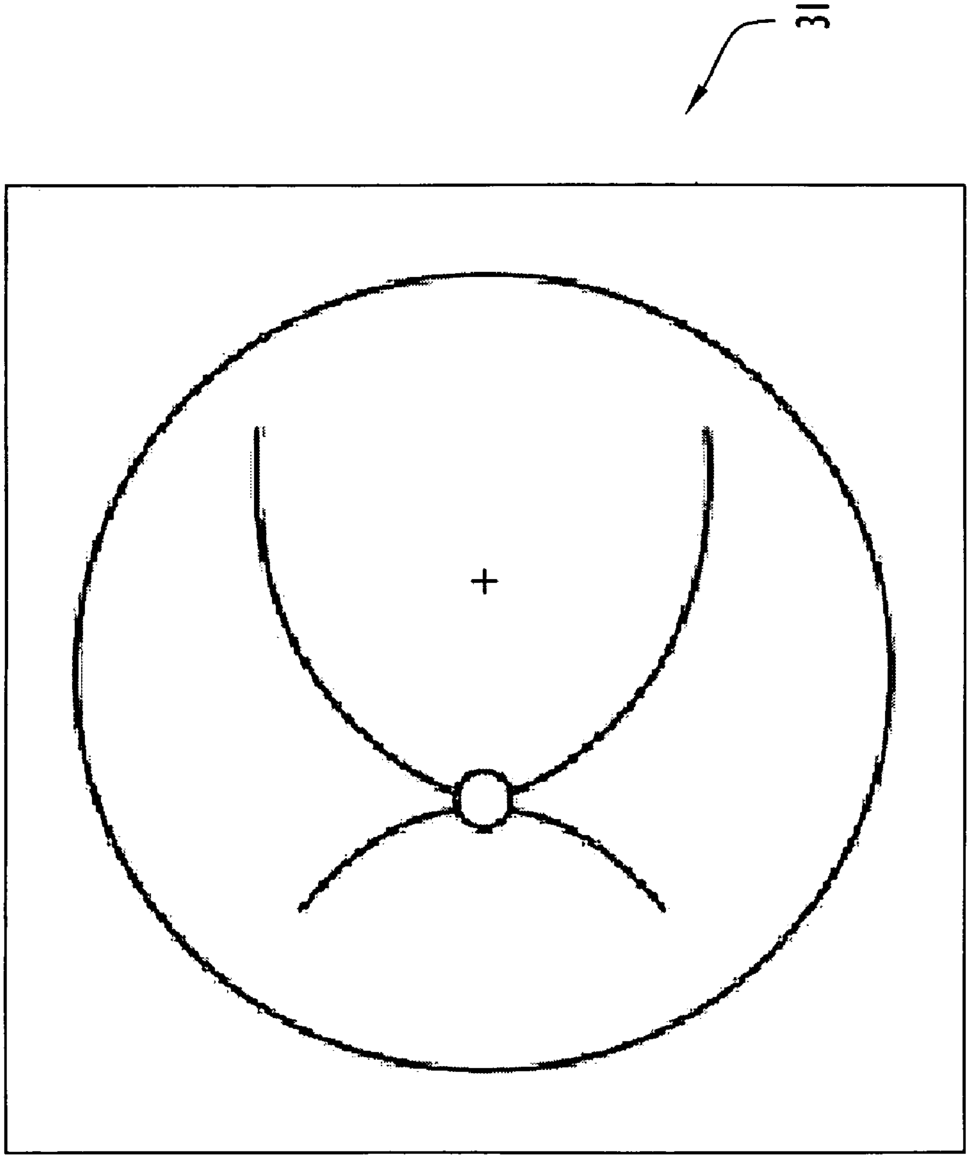
FIG. 14 is a schematic illustration of a template within the graphical user screen of FIG. 5 subsequent a user applying a further zoom feature according to the present invention.

Interface window 30 may further enable a physician to change viewing features of the drawing. For example, the interface window includes font icons 94, 96, refresh icon 100 and zoom icon 101 each disposed toward the top of the window. Font icons 94, 96 respectively enable enlarging and reduction of the font size, while refresh icon 100 removes drawing and annotations from the background image. The refresh basically serves a reset for the drawing providing a background image without any physician markings. The zoom icon enables a physician to zoom in and zoom out to different template or image levels (e.g. disk only, macula only, posterior segment only, etc.). By way of example, the zoom icon may provide various zoom levels to zoom in and out by two, four, six or eight times. The zoom feature is illustrated by way of example in FIGS. 13-14 with respect to a predefined template.

In addition, interface window 30 may include various features for ease of operation. For example, interface window 30 may include drop down lists 106 disposed toward the upper left corner of the window (e.g., as viewed in FIGS. 5-6) providing various shortcuts to system functions. The lists include shortcuts to functions relating to files (e.g., save, open, etc.), patient (e.g., search, create, etc.) and examinations (e.g., search, select, reports, etc.). A physician actuates the appropriate shortcut via mouse or other input device to perform or be directed to windows performing the desired functions. Further, the interface window may include icons 108 disposed below lists 106 similarly serving as shortcuts to various operations (e.g., open or save file, exit, refresh, etc.).

Figure 15:
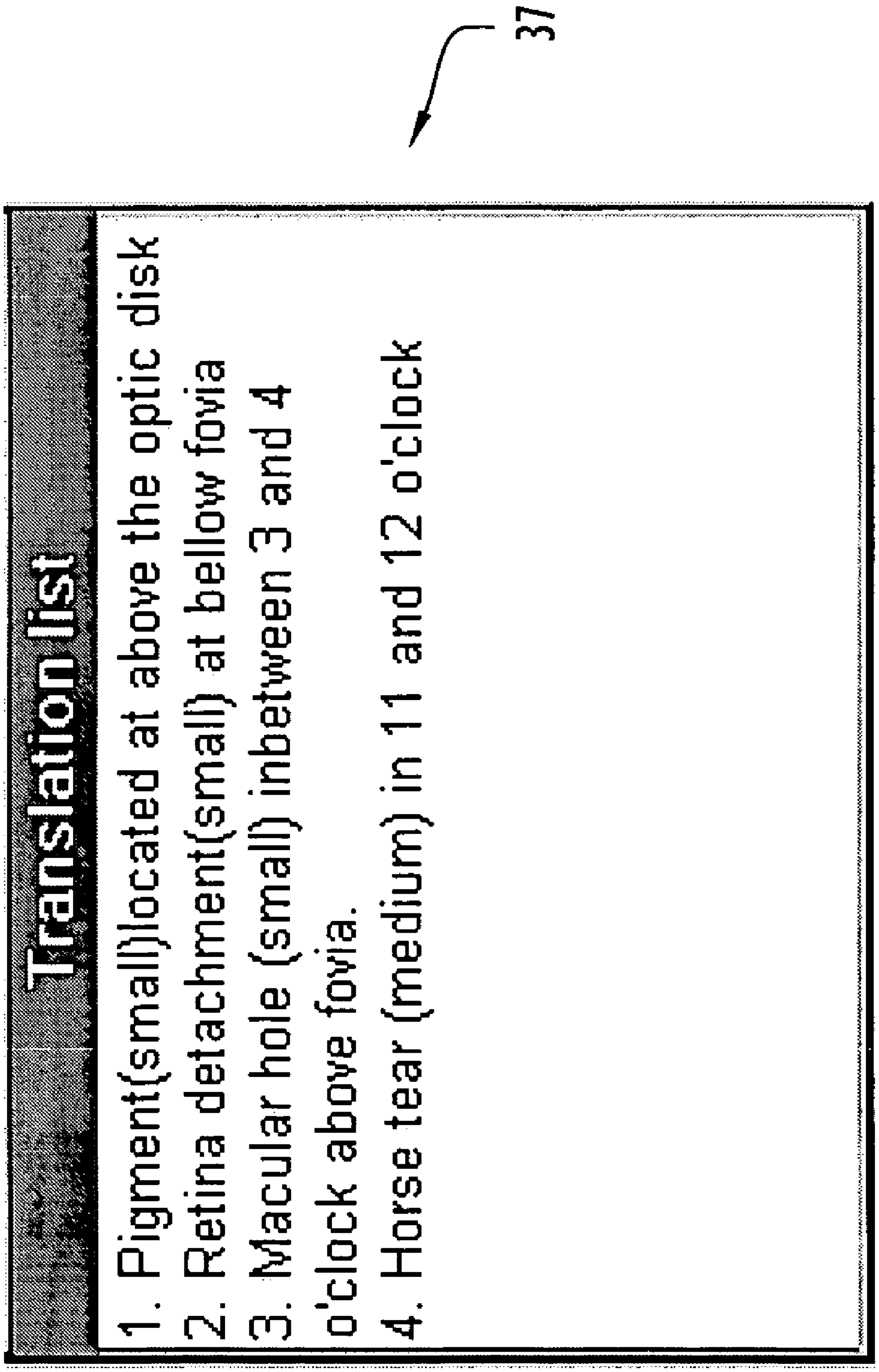
FIG. 15 is a schematic illustration of a portion of the graphical user screen of FIG. 5 including an automatic translation of a physician drawing according to the present invention.

Drawing and annotation module 25 (FIG. 3) also automatically creates annotations 38 in drawing window 31 using annotation data associated with predefined symbols 34. This automated annotation saves the physician time by avoiding the need to annotate the drawing. Exemplary automated annotations 38 are shown in FIG. 7. The physician selects one of the drawing elements or symbols, or freehand drawing and finishes the drawing of one object. The system provides annotations for that symbol automatically, where the physician may validate the drawing practice. The annotation is further updated to an automated translation list described below and displayed within translation list window 37 of interface window 30 (FIGS. 5 and 15). The translation list is referred to when a report is generated by the system as described below.

Each drawing symbol may have an annotation label. However, when the physician places several point symbols on the drawing at one time, the system treats the symbols as a group of point symbols and adds only one annotation label on drawing window 31 as illustrated in FIG. 7 (e.g., the groups of retinal tear, retinal detachment and scleral buckle are each associated with a single annotation label).

The system may utilize various color schemes to represent different problematic areas. For example, the color representation utilized by the system is shown in Table III below. Auto translation module 26 translates physicians drawing activities based on the color representations as described below.

TABLE III

| Color | Description |
|---|---|
| Red | Retinal arteries, attached retina<br>Retinal tear*, Retina hole,<br>Lattice degeneration*,<br>Retinal dialysis, Giant retinal tear,<br>Microanueurysm*, Venous beading,<br>Intraretinal hemorrhage*, Preretinal hemorrhage*,<br>Subhyaloid hemorrhage, Subretinal hemorrhage*,<br>Sub-pigment epithelial hemorrhage*,<br>Retinal neovascularization*,<br>Disk neovascularization*,<br>Optocilliary shunt vessels*, Retinal whitening,<br>Disk edema |
| Red with green operculum | Operculated tear* |
| Blue | Retinal veins, Retinal detachment*, Traction retinal detachment,<br>Retina edema*,<br>Subretinal fluid* |
| Blue | Retinal schisis<br>Outer layer hole, Inner layer hole<br>Demarcation line<br>Cystic retinal tuft<br>Meridonal fold<br>Enclosed ora bay<br>Cobblestone atrophy*<br>Peripheral cystic retinal degeneration<br>Snowbank,<br>Cystoid macular edema* |
| Yellow | Chorioretinal exudates,<br>intraretinal exudates,<br>intraretinal edema,<br>Drusen*, Disciform scar*, Subretinal scarring*,<br>Arteriolar embolus, Vascular sheathing |
| Green | Preretinal opacities*, Asteroid hyalosis,<br>Opacities in media, vitreous Hemorrhage*,<br>Epiretinal membrane,<br>Star-fold, Epiretinal membrane*<br>Weiss ring* |
| Purple | Flat neovascularization |
| Orange | Elevated neovascularization |
| Brown | Retinal pigment epithelium or choroidal pigmentation seen through attached retina; vascular occlusion,<br>Subretinal membrane,<br>Retinal pigment epithelial atrophy*<br>Retinal pigment epithelial pigment hyperplasia*<br>Pigment epithelial mottling*<br>Peripapillary atrophy* |
| Blue outline filled with red | Full thickness sensory retinal break |
| Blue outline cross-hatched with red | Partial thickness sensory retina break |
| Black outline filled with Black lattice pattern | Lattice degeneration of attached retina |
| Blue outline with blue lattice pattern | Lattice degeneration of detached retina |
| Black outline cross-hatched with red | Paving-stone degeneration of attached retina |
| Brown outline cross-hatched with red | Paving-stone degeneration seen through detached retina |
| Blue lines (short) | Retinal tufts and meridional folds |
| Black scalloped line overlying ora serrata circle on fundus chart | Ora serrata with adjacent attached retina |
| Blue scalloped line | Ora serrata with adjacent detached retina |
| White | Cotton-wool spot, Laser scar*, Cryo scar* |
| Green + red | Fibrovascular proliferation*, Retinal striae* |
| Red with cuff of blue | Macular hole*, Psuedohole*, Retinal telangiectasis |

The present invention system typically employs the color arrangement within Table III as a default for the translation. However, the physician may change the color settings manually (e.g., since one color may represent more than one definition).

Auto translation module 26 (FIG. 3) automatically generates statements regarding the data in drawing area 31 for display in translation window 37 (FIGS. 5 and 15). Sample statements are illustrated in FIG. 15. Whenever each drawing is completed, an annotation is automatically inserted into drawing area 31 and displayed as described above. The system maintains annotation keywords for each drawing, which are displayed in translation keyword or statement window 37. The drawing module uses positional data from the background image and context and positional data from the predefined symbols to automatically create the statements shown in the translation list. Textual descriptions based on the translation list are further generated and displayed in symbol window 110 (FIG. 22) under report tab 116 as described above. The textual descriptions are utilized to generate reports as described below.

The auto translation module automatically starts to translate background image and annotation results in accordance with the generated annotations. This technology is based on the translation of Bitmap size, orientation, and Bitmap locations on the background image. Each background image or template symbol has been registered into the system with location information of each object drawn by the physician. The system maintains the grid of each template symbol to find the right location of each object drawn by the physician before starting the translation. The automated translation function commences immediately after the physician finishes the drawing of each symbol. Positive and/or negative medical findings may be presented on the background images or templates with automatic indication of finding locations. The specificity of the finding location information may be varied by a user. For example, the specificity of the location information may be set to a detailed location (e.g., between 1 and 2 o'clock of the posterior region), a general area (e.g., superior temporal posterior region, etc.), or no location information.

The auto translation module maintains the image mapping with the grid to find the exact location of each object drawn. If the physician modifies an already drawn object, the translation list is updated. In this case, the translation of the original drawn object is deleted from the list. A translated list may be modified manually by the physician. The physician may further save the list to invoke report generation module 27 (FIG. 3) to generate reports.

Figure 16:
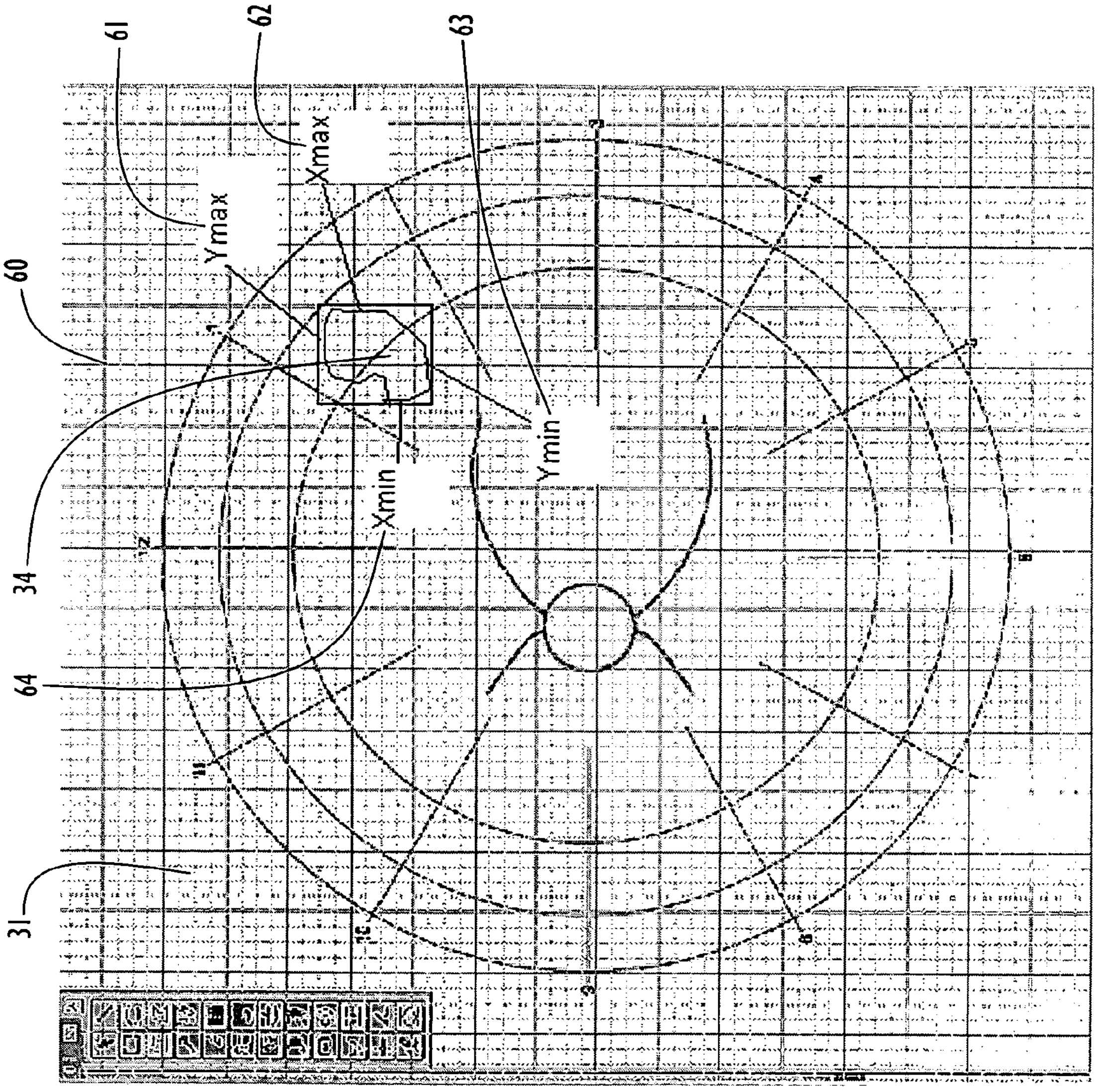
FIG. 16 is an illustration of the manner in which an object location on a selected template is determined for translation according to the present invention.

The manner in which auto translation module 26 determines positional information is illustrated in FIG. 16. Drawing area 31 contains a fine grid 60. The maximum extents of a predefined symbol 34 or other symbol drawn on a background image (e.g., a template as viewed in FIG. 16) are calculated with respect to this grid 60. The positional values saved with each drawn symbol include the maximum vertical value (Ymax) 61, maximum horizontal value (Xmax) 62, the minimum vertical value (Ymin) 63, and the minimum horizontal value (Xmin) 64. The values along with a specific range section of each image template are used in the generation of the positional description of symbol 34. Thus, four locations are utilized to translate an object and annotation (e.g., (Xmin, Ymin), (Xmin, Ymax), (Xmax, Ymin), and (Xmax, Ymax)). In most cases, the drawing for this practice is not required to be accurate. However, if the physician wants to view exact location information and an accurate translation, the system utilizes the location information of each drawn symbol on the background image.

The system maintains all records of each translated object (e.g., Object symbol type, Annotation Note, Object location data (Xmin, Ymin) and (Xmax, Ymax), Manually changed note by physician, Template type, etc.) in the system database. This information can be used to create a report anytime the physician drives the system and without reopening the drawing and annotation package.

Figure 17:
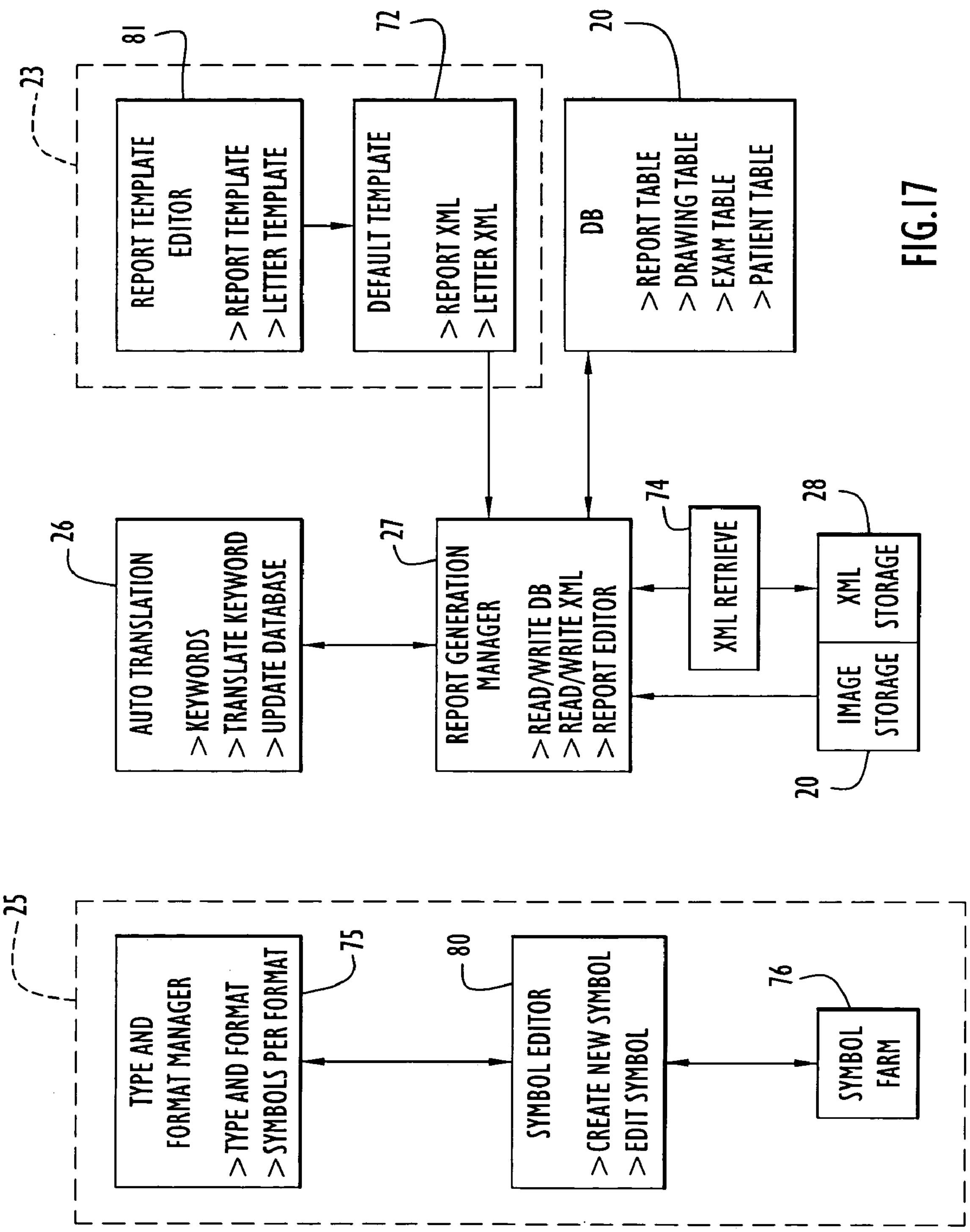
FIG. 17 is a block diagram of system components for drawing and report generation according to the present invention.

Report generation module 27 (FIG. 3) can save the physicians a considerable amount of time by using the keywords or statements generated by translation module 26 to automatically create various types of reports from report templates. The system components for drawing and report generation are illustrated in FIG. 17. Specifically, the components include drawing module 25, auto translation module 26, report generation module 27 and template generation module 23. These components enable the system to manage the database to store drawing results in order to create various reports later. The physician initially can design a customized form of report template using template generation module 23 described below. All the designed formats of a report are automatically generated and saved to an RTF file to enable the physician to utilize this file as a typical document.

Drawing module 25 includes format manager module 78, symbol editor module 80 and symbol store or farm 76 to store symbol information. Each report type is associated with drawing formats. For example, a retina drawing type is associated with separate formats including retina detachment and diabetic retina. When a user selects one of the drawing types and formats, associated symbol types are updated to the symbol window (FIG. 5) as described above by the format manager module. Each symbol shown in the window is used for the most popular forms of drawings.

Reports are generated by the system based on report templates. A report template indicates the arrangement and information desired for a report. Each report format (e.g., retina detachment, etc.) is associated with a default form or template 72 and is typically formatted with XML tags (e.g., as viewed in FIGS. 18A-18C), while the report generation module retrieves the appropriate information (e.g., textual descriptions, translation list, images, etc.) from database 20 (FIGS. 18A-18C show an XML template with retrieved values) and formats the report in accordance with the template.

Basically, the system employs a hierarchical structure, where the XML report template is used as a base file with all values initialized to null. When the system generates a report, the report generation module retrieves the empty XML file from storage 28, via a retrieve/storage module 74, and obtains the necessary information from database 20 to provide values for the null fields in the XML file. Therefore, only one XML file exists as an empty report template.

The XML file name for a completed report is typically changed in accordance with various patient characteristics (e.g., patient name, drawing and report date, drawing type, format name, etc.) and stored to an examination image storage directory within XML storage 28. Thus, the resulting report document (e.g., RTF or .doc file) is generated by report module 27 based on the XML report template and drawing record in the system database. Exemplary reports in the form of a medical report and a letter are respectively illustrated in FIGS. 19 and 20A-20B. In addition, the present invention system may automatically, or enable physicians to, add images or drawings to generated reports as described below.

The physician can modify the default report format or template. In particular, template generation module 23 includes template editor module 81. The editor module enables the physician to edit or create reports or report templates, where the templates are stored in XML configuration module 28 as a type of XML template to enable template generation and editing. The template editor module enables physicians to create customized reports by specifying fixed text and programmable fields. The fixed text always remains the same between different patients or examinations, while the programmable fields are filled in from data associated with each particular drawing, examination or patient as described above.

Template generation module 23 employs a user interface (e.g., window, screens, etc.) to enable the physician to edit or create a report template (e.g., arrange the report, select information to be placed in the report, etc.). A report template window enables a user to edit the format of a report (e.g., add more description or notes on the report format, insert custom data, etc.). This function is designed with XML technology to maintain the desired format for each customer, where the physicians may utilize any quantity of formats. The report template window includes tabbed sections each corresponding to a report format. A button on the window actuates the template editor for the appropriate report. Each tab includes this button to modify the template of each report. This enables physicians to freely modify the predefined template for generating reports in accordance with the physician preference. Only one report template can be generated for each report tab. However, the physician may create a new report type, where additional buttons may be provided for the newly created report type.

A resulting report template is stored in XML configuration module 28. Report module 27 retrieves the appropriate templates to produce reports and provides the desired information. The physician can generate several templates for each kind of drawing. All the reports associated with a type of drawing are created when the drawing is completed. Once the drawing is completed and a physician saves the drawing as described above, the system displays various custom reports to the physician for selection and generation by report module 27 as described above. The reports may include: medical drawing reports, referral notes, medical letters, billing information (e.g., for insurance companies), a proofsheet in a patient chart, etc.

Figure 23A:
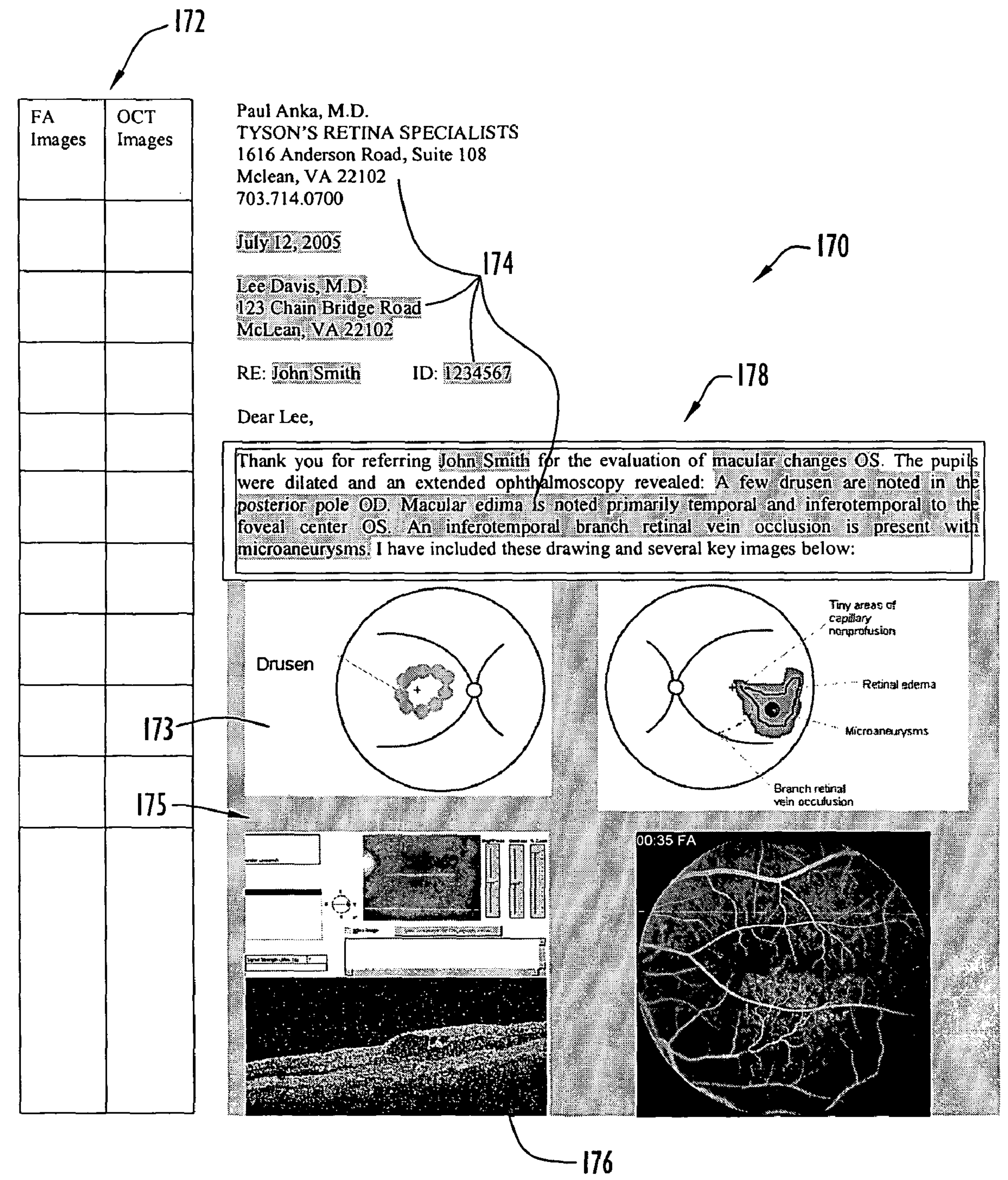

Report module 27 further includes a report editor module. The report editor module enables physicians to edit a report generated from the XML template as illustrated by way of example in FIGS. 23A-23B. Specifically, a report is generated from the appropriate XML template as described above. The report editor module displays an edit window 170 with an image window table 172 and a report area 178. The image window is disposed on the left portion of edit window 170 (e.g., as viewed in FIG. 23A) and includes a series of thumbnail medical images arranged in the form of a table with each column associated with a particular type of examination. By way of example only, image window 172 includes examinations for FA and OCT. However, any other examination images may be included in the image window.

Report area 178 includes the report generated from the associated XML template as described above. The report includes various text fields 174 and image fields 175. The report editor module enables the physician to edit portions of the text fields and select images from image window 172 for insertion into report image fields 175. In particular, report text fields 174 include text in accordance with the XML template (e.g., specific text to be included in the report), text generated by the system (e.g., annotations, translation list, patient, examination or other information from the database, etc.) and text provided by the physician. The report editor module enables the physician to modify the text generated by the system (e.g., highlighted text in FIGS. 23A-23B) and provided by the physician to produce a desired report.

In addition, the physician may select an image from image window 172 for insertion into image field 175. The image field includes annotated drawing field 173 and selected image field 176. Field 173 displays annotated images generated by the physician via the system, while field 176 displays images selected by the physician from image window 172. The physician selects the desired images from image window 172 (e.g., via mouse or other input device such as a digital pen) and the system inserts the selected images into image field 176. This enables the physician to place actual medical images near the annotated drawings in the report. The report editor module may enable editing of any desired text or image fields. The report editor module may permit a physician to modify or view a report automatically after a report is generated. Alternatively, the report editor module may be invoked from interface window 30 (FIG. 5) via drop down lists 106 or shortcuts 108.

History data management module 24 (FIG. 3) provides a listing of previous drawings and annotations. This module basically manages saved annotations and reports and enables display of a history drawing list in history window 90 as illustrated in FIG. 21. The drawing directory list enables the physician to load previous drawings and annotations on drawing area 31 by actuating a load icon 92 associated with a desired drawing. If the physician clicks one of the old historic drawing records and there are other older exams, the system selects each of the related drawing history files and overlays the drawing and annotations into drawing area 31. In this case, the physician can easily view the historic drawings and recognize the old drawing history by the time selected. If the physician selects the latest drawing record, the system will display all the drawing records on the history window to enable the physician to view all the drawings in an overlaid fashion.

Figure 1:
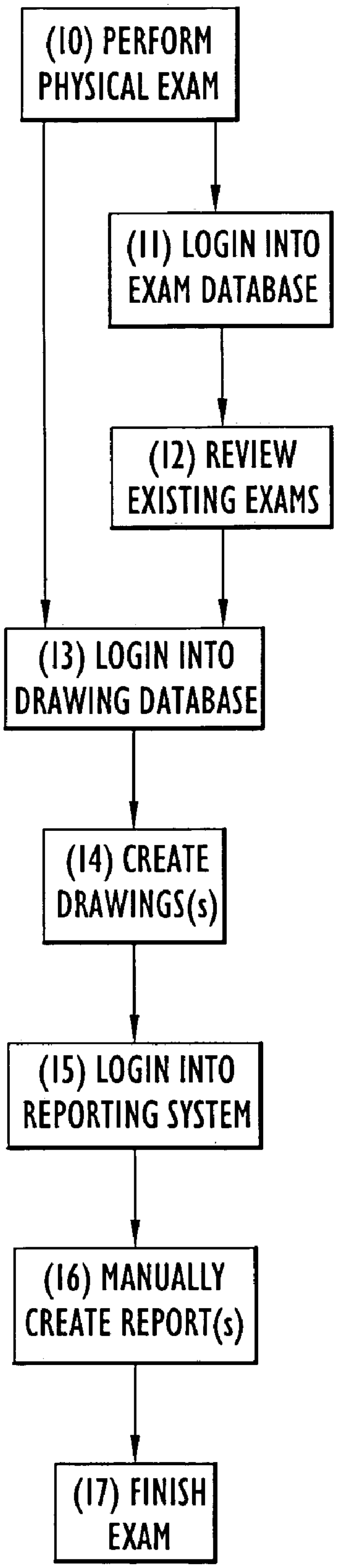
FIG. 1 is a procedural flow chart illustrating the workflow with independent, stand-alone drawing and report generation systems.
Figure 2:
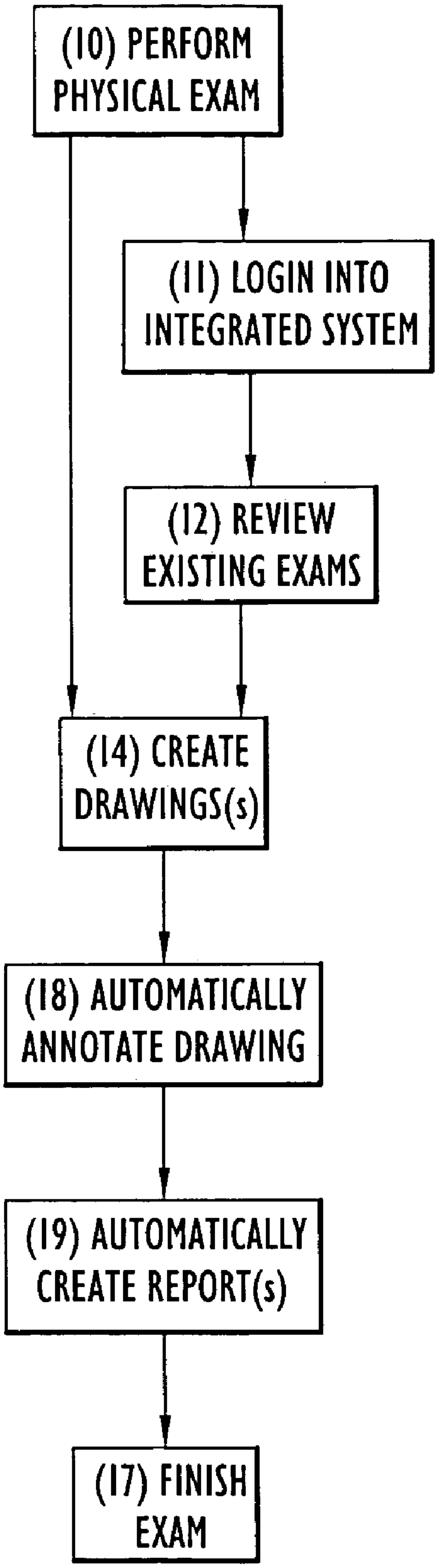
FIG. 2 is a procedural flow chart illustrating the enhanced workflow of an integrated imaging and automated report generation system according to the present invention.

The combined image, drawing and report management system of the present invention greatly simplifies the physicians' workflow (FIG. 2) as compared to the workflow described for the independent stand-alone systems (FIG. 1). The workflow of the present invention is described with reference to FIG. 2. Specifically, the physician performs a manual examination of the eye at step 10. If the patient is a repeat patient or has already had images taken, the physician logs into the integrated system at step 11, and retrieves and reviews existing examinations at step 12. The physician searches for existing drawings to modify or create and saves the drawings from scratch at step 14. All the remaining steps are performed automatically by the present invention system. In particular, the system automatically annotates the drawing at step 18 and creates the drawing statements and the drawing specific reports at step 19. The physician can then finish the examination at step 17, and go on to other tasks.

It will be appreciated that the embodiments described above and illustrated in the drawings represent only a few of the many ways of implementing a system and method for automated report generation of ophthalmic examinations from digital drawings.

The present invention system may be implemented by any quantity of any personal or other type of computer or processing system (e.g., IBM-compatible, Apple, Macintosh, laptop, palm pilot, etc.). The computer system may include any commercially available operating system (e.g., Windows, OS/2, Unix, Linux, etc.). The computer system may further include any commercially available or custom software (e.g., server software, browser software, viewing software, etc.), database and/or database management systems. The computer system may further include any types of input devices (e.g., keyboard, mouse, voice recognition, light or other pens, etc.) to navigate the screens, draw elements, enter information and/or actuate buttons or icons. The databases, stores or other storage units may be implemented by any conventional or other database or storage structure (e.g., file, data structure, memories, etc.).

It is to be understood that the software for the computer system may be implemented in any desired computer language and could be developed by one of ordinary skill in the computer arts based on the functional descriptions contained in the specification and illustrated in the drawings. By way of example only, the software of the present invention may be developed utilizing JAVA Script, HTML, Visual Basic Script, MS C#, .NET Technology and/or C++ computer languages. The computer system may alternatively be implemented by any type of hardware and/or other processing circuitry. The various functions of the computer system may be distributed in any manner among any quantity of software modules, processing or computer systems and/or circuitry. The software and/or algorithms described above and illustrated in the flow chart may be modified in any manner that accomplishes the functions described herein.

The network may be implemented by any communications network (e.g., LAN, WAN, Internet, Intranet, etc.). The computer system may include any conventional or other communications devices to communicate over the network via any conventional or other protocols. The functions of the computer system may be distributed among a server and/or end-user systems in any desired fashion.

The display screens, windows and reports may be arranged in any fashion and contain any type of information (e.g., images of any desired human or animal anatomy (e.g., eye, etc.), images of any tests, etc.). The screens may include any quantity of any type of buttons, icons and/or symbols of any shapes or sizes disposed at any locations to display information and/or initiate any desired actions. The screens may include any quantity of any type of fields (e.g., fill in, drop down menus or lists, etc.), areas or sub windows of any shapes or sizes disposed at any locations to receive information from the system and/or user and/or to display information. The areas or sub-windows may include any quantity of tabs or other dividers to partition the areas in any desired fashion based on any characteristics. The system may automatically log out a user after any desired time interval. The system may display and/or receive information via any input mechanisms (e.g., screens, menus, line prompts, forms, fields, etc.).

The system may enable selection of any quantity of any type of background image (e.g., medical or other image, photograph, photograph composite, templates, etc.) for drawing. The physician or other user may draw any types of objects (e.g., shapes, text, lines, etc.) on the selected background image at any desired locations. The system may employ any conventional or other marking or drawing tools (e.g., conventional paint functions, etc.). The markings may be saved independent of or along with the background image. A saved drawing may be retrieved for viewing and/or editing at any desired time. The symbols may be of any shape, size, quantity or color and may represent any desired disease or problematic area. The symbols may further indicate a positive medical finding (e.g., a healthy body portion or lack of a disease). The symbols may be associated with further modifiers of any size, shape or color and representing any further diseases or problems (e.g., a combination of diseases) or positive medical findings. The symbols may be selected via any suitable techniques (e.g., selection via an input device, text search, etc.). The symbol window may be arranged in any fashion and include any desired symbols categorized in any fashion.

The system may provide predefined symbols and/or permit a user to create custom symbols. The system may enable designation of any suitable characteristics for a custom symbol (e.g., shape size, fill pattern, outline color, line thickness and/or type, etc.). Symbols may be drawn by the system based on designation of any quantity of any suitable points from a physician or other user (e.g., end-points, etc.). The system may enable drawing of open or closed shapes, where the closed shape may be automatically closed by the system via any type of element (e.g., line, curve, arc, user defined linear or other shape, etc.). The system may orient selected symbols on the background image in any desired fashion (e.g., toward the image center, toward user defined or specified points or locations, etc.).

The interface window may alter any desired characteristics of the selected image and/or drawing for viewing (e.g., zoom, symbol size, font size, etc.). The zoom may zoom in or out by any desired amount (e.g., two times, four times, six times, eight times, etc.). The proofsheet may include any quantity of any desired medical images (e.g., any medical tests, any body portions, etc.).

The examination table may be arranged in any fashion and include any information listed in any desired order (e.g., based on any information). The search may be performed based on any desired searching criteria (e.g., any table or database field, dates or range of dates, etc.). The table entries may be sorted in any desired fashion or order based on any quantity of any desired table columns.

The system may display any quantity of images or patient information in any desired fashion. Selection of items (e.g., symbols, images, etc.) may be accomplished via any conventional or other techniques (e.g., any quantity of mouse clicks, light or other pen, voice recognition, etc.). The system may annotate drawings based on any desired criteria (e.g., color, symbol size, symbol location, symbol type, etc.). The location of the symbol on the background image may be determined based on any suitable quantity of points within any desired coordinate system (e.g., Polar, Cartesian, etc.). The system may employ any type of location scheme (e.g., grid, pixel counts, etc.). The annotation may include any desired information and be disposed at any suitable location on the background image. The system may utilize the annotation to generate textual or other statements in any desired fashion (e.g., predefined text for insertion of annotation, generate statements based on criteria or conditions, etc.).

The report templates may be arranged in any desired format and include any desired information (e.g., text, etc.). The template may include any quantity of fields to receive any desired information from the system (e.g., patient, doctor, hospital, etc.). The templates may be implemented in any suitable language or by any suitable structures (e.g., XML, forms, etc.).

The reports may be arranged in any desired format and include any desired information (e.g., text, images, drawings, etc.). The report may be in the form of any type of document (e.g., letter to insurance company, clinic notes, physician report, referral letter, etc.). The report may include any positive or negative medical findings, and report the location of areas with any desired specificity as indicated by the user. The specificity may be indicated in any desired levels (e.g., specific, general two or three dimensional locations, no location information, etc.). The report may be edited by a user in any fashion (e.g., change text, add or remove images, etc.).

The system may display any quantity of prior drawings to a user for selection based on any criteria (e.g., patient, examination, dates, etc.). The system may display any quantity of drawings from a related set (e.g., based on time or other precedence) in any fashion (e.g., overlaid fashion, etc.) based on a user selection of at least one of the related drawings. The windows or screens may be navigated in any desired order in response to any suitable actions (e.g., buttons, shortcuts, drop down lists, selections, etc.).

The present invention system may include any type of wireless or other sensing device to detect medical personnel. The medical personnel may include any type of wireless or other device to enable detection by the system (e.g., stand-alone system or remote end-user) and to provide information to the system. The information may enable any desired system action (e.g., automatic login, searching, etc.). Further, the wireless card may be in the form of a remote processing device (e.g., PDA, etc.) to enable remote access to the system.

The software of the present invention system may be available on a recorded medium (e.g., magnetic or optical mediums, magneto-optic mediums, floppy diskettes, CD-ROM, DVD, memory devices, etc.) for use on stand-alone systems or systems connected by a network or other communications medium, and/or may be downloaded (e.g., in the form of carrier waves, packets, etc.) to systems via a network or other communications medium.

It is to be understood that the terms “top”, “bottom”, “side”, “upper”, “lower”, “front”, “rear”, “horizontal”, “vertical”, “right”, “left” and the like are used herein merely to describe points of reference and do not limit the present invention to any specific configuration or orientation.

The present invention may be utilized for any type of medical or other application and by any user (e.g., physician, medical personnel, patients, administrative or other assistants, etc.) to enable generation of reports from annotated images. The system may be a stand-alone or networked system, or may be combined or embedded within other systems, such as the system disclosed in the aforementioned patent applications.

From the foregoing description, it will be appreciated that the invention makes available a novel system and method for automated report generation of ophthalmic examinations from digital drawings, wherein a digital medical reporting system automatically generates various patient reports from ophthalmic drawings based on manual evaluation of the interior of the eye and/or other images generated from image capture stations.

Having described preferred embodiments of a new and improved system and method for automated report generation of ophthalmic examinations from digital drawings, it is believed that other modifications, variations and changes will be suggested to those skilled in the art in view of the teachings set forth herein. It is therefore to be understood that all such variations, modifications and changes are believed to fall within the scope of the present invention as defined by the appended claims.

What is claimed is:

1. A system to produce reports from medical drawings comprising:

a computer system to enable a user to produce a medical drawing and to examine that drawing and generate a report, said computer system including:

an image display module to display a user interface and enable selection of a background medical image by said user;

a drawing module to display said selected background image and facilitate selection and placement of at least one symbol by said user on said selected background image, wherein each said selected symbol on said selected background image identifies a corresponding medical condition within that background image;

a translation module to examine said user drawing and automatically generate a textual annotation for each said medical condition identified by said at least one selected symbol for display to label that medical condition on said selected background image and one or more textual statements based on said at least one selected symbol within said selected background image; and a report module to generate a report indicating said medical conditions identified by said at least one selected symbol based on said textual statements generated from said user drawing providing characteristics of said medical conditions.

2. The system of claim 1, wherein said background image includes ophthalmic images.

3. The system of claim 1, wherein said background image is one of a medical image and a predefined template.

4. The system of claim 1 further including:

a storage unit to store information relating to at least patients and examinations;

wherein said computer system further includes:

a search module to retrieve patient examinations stored within said storage unit in accordance with search criteria including at least one of date information, patient information and examination information.

5. The system of claim 1, wherein said drawing module includes:

an update module to retrieve a previously generated drawing and facilitate modifications to said retrieved drawing to enable said user to update medical conditions within said background image.

6. The system of claim 1, wherein said drawing module includes:

a symbol module to display at least one symbol each associated with a medical condition for selection and placement on said selected background image.

7. The system of claim 6, wherein said symbol module includes:

a symbol generation module to create a custom symbol in accordance with user specified characteristics and associate said custom symbol with corresponding information including at least one of a textual description, a symbol category and a symbol type.

8. The system of claim 6, wherein each symbol is associated with one of a positive and negative medical condition.

9. The system of claim 6, wherein said symbol module includes:

a symbol placement module to place a selected symbol on said selected background image in accordance with position points indicated by said user on that background image.

10. The system of claim 1, wherein said drawing module includes:

a zoom module to adjust magnification of said displayed background image.

11. The system of claim 1, wherein said report module includes:

a report generation module to generate said report in accordance with a report template.

12. The system of claim 11, wherein said report module further includes:

a template module to create said report template in accordance with user specified characteristics to produce custom reports.

13. The system of claim 11, wherein said translation module includes:

a statement module to translate said user drawing into said one or more textual statements;

wherein said report generation module generates said report based on said statements and in accordance with said report template.

14. The system of claim 11, wherein said report template indicates at least one of positive and negative medical findings.

15. The system of claim 1, wherein said drawing module includes:

a location module to determine locations of identified medical conditions on said selected background image for said report.

16. The system of claim 1, wherein said report module includes:

an image module to insert at least one of images and drawings within said generated report.

17. The system of claim 1, wherein said report is in the form of one of a medical drawing report, a referral letter, a medical letter, a billing report for an insurance company and a proof-sheet of images for a patient chart.

18. A computer-implemented method of producing reports from medical drawings generated by users via a computer system comprising:

(a) displaying a user interface and enabling selection of a background medical image by a user;

(b) displaying said selected background image and facilitating selection and placement of at least one symbol by said user on said selected background image, wherein each said selected symbol on said selected background image identifies a corresponding medical condition within that background image;

(c) examining said user drawing and automatically generating a textual annotation for each said medical condition identified by said at least one selected symbol for display to label that medical condition on said selected background image and one or more textual statements based on said at least one selected symbol within said selected background image; and (d) generating a report indicating said medical conditions identified by said at least one selected symbol based on said textual statements generated from said user drawing providing characteristics of said medical conditions.

19. The method of claim 18, wherein said background image includes ophthalmic images.

20. The method of claim 18, wherein said background image is one of a medical image and a predefined template.

21. The method of claim 18, wherein said computer system includes a storage unit to store information relating to at least patients and examinations, and step (a) further includes:

(a.1) retrieving patient examinations stored within said storage unit in accordance with search criteria including at least one of date information, patient information and examination information.

22. The method of claim 18, wherein step (b) further includes:

(b.1) retrieving a previously generated drawing and facilitating modifications to said retrieved drawing to enable said user to update medical conditions within said background image.

23. The method of claim 18, wherein step (b) further includes:

(b.1) displaying at least one symbol each associated with a medical condition for selection and placement on said selected background image.

24. The method of claim 23, wherein step (b.1) further includes:

(b.1.1) creating a custom symbol in accordance with user specified characteristics and associating said custom symbol with corresponding information including at least one of a textual description, a symbol category and a symbol type.

25. The method of claim 23, wherein each symbol is associated with one of a positive and negative medical condition.

26. The method of claim 23, wherein step (b) further includes:

(b.2) placing a selected symbol on said selected background image in accordance with position points indicated by said user on that background image.

27. The method of claim 18, wherein step (b) further includes:

(b.1) adjusting magnification of said displayed background image.

28. The method of claim 18, wherein step (d) further includes:

(d.1) generating said report in accordance with a report template.

29. The method of claim 28, wherein step (d.1) further includes:

(d.1.1) creating said report template in accordance with user specified characteristics to produce custom reports.

30. The method of claim 28, wherein step (c) further includes:

(c.1) translating said user drawing into said one or more textual statements; and step (d.1) further includes:

(d.1.1) generating said report based on said statements and in accordance with said report template.

31. The method of claim 28, wherein said report template indicates at least one of positive and negative medical findings.

32. The method of claim 18, wherein step (b) further includes:

(b.1) determining locations of identified medical conditions on said selected background image for said report.

33. The method of claim 18, wherein step (d) further includes:

(d.1) inserting at least one of images and drawings within said generated report.

34. The method of claim 18, wherein said report is in the form of one of a medical drawing report, a referral letter, a medical letter, a billing report for an insurance company and a proofsheet of images for a patient chart.

35. A program product apparatus including a computer readable medium with computer program logic recorded thereon for producing reports from medical drawings, said program product apparatus comprising:

an image display module to display a user interface and enable selection of a background medical image by said user;

a drawing module to display said selected background image and facilitate selection and placement of at least one symbol by said user on said selected background image, wherein each said selected symbol on said selected background image identifies a corresponding medical condition within that background image;

a translation module to examine said user drawing and automatically generate a textual annotation for each said medical condition identified by said at least one selected symbol for display to label that medical condition on said selected background image and one or more textual statements based on said at least one selected symbol within said selected background image; and a report module to generate a report indicating said medical conditions identified by said at least one selected symbol based on said textual statements generated from said user drawing providing characteristics of said medical conditions.

36. The apparatus of claim 35, wherein said background image includes ophthalmic images.

37. The apparatus of claim 35, wherein said drawing module includes:

a symbol module to display at least one symbol each associated with a medical condition for selection and placement on said selected background image.

38. The apparatus of claim 37, wherein said symbol module includes:

a symbol generation module to create a custom symbol in accordance with user specified characteristics and associate said custom symbol with corresponding information including at least one of a textual description, a symbol category and a symbol type.

39. The apparatus of claim 37, wherein said symbol module includes:

a symbol placement module to place a selected symbol on said selected background image in accordance with position points indicated by said user on that background image.

40. The apparatus of claim 35, wherein said report module includes:

a report generation module to generate said report in accordance with a report template.

41. The apparatus of claim 40, wherein said report module further includes:

a template module to create said report template in accordance with user specified characteristics to produce custom reports.

42. The apparatus of claim 35, wherein said drawing module includes:

a location module to determine locations of identified medical conditions on said selected background image for said report.

43. The apparatus of claim 35, wherein said report is in the form of one of a medical drawing report, a referral letter, a medical letter, a billing report for an insurance company and a proofsheet of images for a patient chart.

44. A system to produce reports from medical drawings comprising:

a computer system to enable a user to produce a medical drawing and to examine that drawing and generate a report, said computer system including:

an image display module to display a user interface and enable selection of a background medical image by said user;

a drawing module to display said selected background image and facilitate selection and placement of at least one identifier by said user on said selected background image, wherein each said selected identifier on said selected background image identifies a corresponding medical condition within that background image;

a translation module to examine said user drawing and generate information based on said at least one selected identifier within said selected background image; and a report module to generate a report indicating said identified medical conditions based on said information generated from said user drawing.

45. The system of claim 44, wherein said background image includes ophthalmic images, and said report is in the form of one of a medical drawing report, a referral letter, a medical letter, a billing report for an insurance company and a proofsheet of images for a patient chart.

46. A computer-implemented method of producing reports from medical drawings generated by users via a computer system comprising:

(a) displaying a user interface and enabling selection of a background medical image by a user;

(b) displaying said selected background image and facilitating selection and placement of at least one identifier by said user on said selected background image, wherein each said selected identifier on said selected background image identifies a corresponding medical condition within that background image;

(c) examining said user drawing and generating information based on said at least one selected identifier within said selected background image; and (d) generating a report indicating said identified medical conditions based on said information generated from said user drawing.

47. The method of claim 46, wherein said background image includes ophthalmic images, and said report is in the form of one of a medical drawing report, a referral letter, a medical letter, a billing report for an insurance company and a proofsheet of images for a patient chart.

48. A program product apparatus including a computer readable medium with computer program logic recorded thereon for producing reports from medical drawings, said program product apparatus comprising:

an image display module to display a user interface and enable selection of a background medical image by said user;

a drawing module to display said selected background image and facilitate selection and placement of at least one identifier by said user on said selected background image, wherein each said selected identifier on said selected background image identifies a corresponding medical condition within that background image;

a translation module to examine said user drawing and generate information based on said at least one selected identifier within said selected background image; and a report module to generate a report indicating said identified medical conditions based on said information generated from said user drawing.

49. The apparatus of claim 48, wherein said background image includes ophthalmic images, and said report is in the form of one of a medical drawing report, a referral letter, a medical letter, a billing report for an insurance company and a proofsheet of images for a patient chart.

* * * * *

UNITED STATES PATENT AND TRADEMARK OFFICE

CERTIFICATE OF CORRECTION

PATENT NO. : 7,793,217 B1
APPLICATION NO. : 11/202371
DATED : September 7, 2010
INVENTOR(S) : Young Kim et al.

It is certified that error appears in the above-identified patent and that said Letters Patent is hereby corrected as shown below:

Column 1, line 32, replace “eye (Opthalmoscopy)” with -- eye (Ophthalmoscopy) --;
lines 49 and 50, replace “Laser Opthalmoscope” with -- Laser Ophthalmoscope --;
Column 2, line 1, replace “Opthalmoscopy (drawing)” with -- Ophthalmoscopy (drawing) --;
Column 4, line 61, replace “opthalmology system” with -- ophthalmology system --; and
Column 8, line 27, replace “Opthalmology area” with -- Ophthalmology area --.

Signed and Sealed this
Twenty-third Day of August, 2011

David J. Kappos
*Director of the United States Patent and Trademark Office*